US012623055B2

(12) United States Patent

McLaughlin et al.

(10) Patent No.: US 12,623,055 B2

(45) Date of Patent: *May 12, 2026

(54) FIBER OPTICS OXIMETRY SYSTEM FOR DETECTION AND CONFIRMATION

(71) Applicant: Bard Access Systems, Inc., Salt Lake City, UT (US)

(72) Inventors: William Robert McLaughlin, Bountiful, UT (US); Steffan Sowards, Salt Lake City, UT (US); Anthony K. Misener, Bountiful, UT (US); Shayne Messerly, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/792,277

(22) Filed: Aug. 1, 2024

(65) Prior Publication Data

US 2024/0390644 A1      Nov. 28, 2024

Related U.S. Application Data

(63) Continuation of application No. 17/484,960, filed on Sep. 24, 2021, now Pat. No. 12,064,569.

(Continued)

(51) Int. Cl.
*A61M 25/01*        (2006.01)
*H01R 13/52*        (2006.01)

(52) U.S. Cl.
CPC ..... *A61M 25/0102* (2013.01); *A61M 25/0111* (2013.01); *H01R 13/5224* (2013.01); *A61B 2562/227* (2013.01); *H01R 2201/12* (2013.01)

(58) Field of Classification Search
CPC ........ A61B 2560/066; A61B 2562/227; A61B 5/061; A61B 5/065; A61B 5/14552;

(Continued)

(56) References Cited

U.S. PATENT DOCUMENTS

| 4,813,429 A | 3/1989 | Eshel et al. |
| 5,099,845 A | 3/1992 | Besz et al. |

(Continued)

FOREIGN PATENT DOCUMENTS

| CN | 101132730 A | 2/2008 |
| CN | 111265309 A | 6/2020 |

(Continued)

OTHER PUBLICATIONS

Mayoral et al. Fiber Optic Sensors for Vital Signs Monitoring. A Review of Its Practicality in the Health Field. Biosensors (Basel). Feb. 23, 2021;11(2):58. doi: 10.3390/bios11020058.

(Continued)

*Primary Examiner* — Amelie R Davis

(74) *Attorney, Agent, or Firm* — Rutan & Tucker LLP

(57) ABSTRACT

A system, apparatus and method directed to placing a medical instrument in a vasculature of a patient body, the system including an optical fiber with one or more core fibers. The system can include a console having non-transitory computer-readable medium storing logic that, when executed, causes operations of providing an incident light signal to the optical fiber, receiving a reflected light signal of the incident light, wherein the reflected light signal is reflected from at least one of red blood cells or tissue within the patient body, processing the reflected light signal to determine an oxygen level within the patient body near a distal tip of the optical fiber. The method can include determining a location of the distal tip of the optical fiber within the patient body at least based on the oxygen level.

13 Claims, 13 Drawing Sheets

Related U.S. Application Data

(60) Provisional application No. 63/083,457, filed on Sep. 25, 2020.

(58) Field of Classification Search
CPC ... A61B 5/1459; A61B 5/6849; A61B 5/6851; A61M 25/0102; A61M 25/0111
See application file for complete search history.

(56) References Cited

U.S. PATENT DOCUMENTS

| | | | |
|---|---|---|---|
| 5,163,935 A | 11/1992 | Black et al. |
| 5,207,672 A | 5/1993 | Roth et al. |
| 5,211,165 A | 5/1993 | Dumoulin et al. |
| 5,275,151 A | 1/1994 | Shockey et al. |
| 5,280,786 A | 1/1994 | Wlodarczyk et al. |
| 5,423,321 A | 6/1995 | Fontenot |
| 5,454,807 A | 10/1995 | Lennox et al. |
| 5,460,182 A | 10/1995 | Goodman et al. |
| 5,517,997 A | 5/1996 | Fontenot |
| 5,622,170 A | 4/1997 | Schulz |
| 5,645,065 A | 7/1997 | Shapiro et al. |
| 5,740,808 A | 4/1998 | Panescu et al. |
| 5,841,131 A | 11/1998 | Schroeder et al. |
| 5,860,923 A | 1/1999 | Lenker et al. |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 6,006,134 A | 12/1999 | Hill et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,245,103 B1 | 6/2001 | Stinson |
| 6,319,227 B1 | 11/2001 | Mansouri-Ruiz |
| 6,343,227 B1 | 1/2002 | Crowley |
| 6,361,545 B1 | 3/2002 | Macoviak et al. |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,650,923 B1 | 11/2003 | Lesh et al. |
| 6,673,214 B1 | 1/2004 | Marchitto et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,060,687 B2 | 6/2015 | Yamanaka et al. |
| 9,114,226 B1 | 8/2015 | Lash et al. |
| 9,206,309 B2 | 12/2015 | Appleby et al. |
| 9,360,630 B2 | 6/2016 | Jenner et al. |
| 9,504,392 B2 | 11/2016 | Caron et al. |
| 9,560,954 B2 | 2/2017 | Jacobs et al. |
| 9,622,706 B2 | 4/2017 | Dick et al. |
| 9,678,275 B1 | 6/2017 | Griffin |
| 10,231,753 B2 | 3/2019 | Burnside et al. |
| 10,258,240 B1 | 4/2019 | Eberle et al. |
| 10,327,830 B2 | 6/2019 | Grant et al. |
| 10,349,890 B2 | 7/2019 | Misener et al. |
| 10,492,876 B2 | 12/2019 | Anastassiou et al. |
| 10,568,586 B2 | 2/2020 | Begin et al. |
| 10,631,718 B2 | 4/2020 | Petroff et al. |
| 10,992,078 B2 | 4/2021 | Thompson et al. |
| 11,123,047 B2 | 9/2021 | Jaffer et al. |
| 11,525,670 B2 | 12/2022 | Messerly et al. |
| 11,656,140 B1 | 5/2023 | Miller |
| 2001/0014793 A1 | 8/2001 | Brugger et al. |
| 2002/0198457 A1 | 12/2002 | Tearney et al. |
| 2003/0092995 A1 | 5/2003 | Thompson |
| 2004/0129555 A1 | 7/2004 | Marchitto et al. |
| 2004/0143183 A1 | 7/2004 | Toyoda et al. |
| 2004/0161362 A1 | 8/2004 | Bogert |
| 2004/0242995 A1 | 12/2004 | Maschke |
| 2005/0033264 A1 | 2/2005 | Redinger |
| 2005/0163424 A1 | 7/2005 | Chen |
| 2005/0228221 A1 | 10/2005 | Hirakawa |
| 2005/0251017 A1 | 11/2005 | Azar |
| 2005/0261598 A1 | 11/2005 | Banet et al. |
| 2005/0278010 A1 | 12/2005 | Richardson |
| 2006/0013523 A1 | 1/2006 | Childlers et al. |
| 2006/0015136 A1 | 1/2006 | Besselink |
| 2006/0036164 A1 | 2/2006 | Wilson et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0156019 A1 | 7/2007 | Larkin et al. |
| 2007/0201793 A1 | 8/2007 | Askins et al. |
| 2007/0238922 A1 | 10/2007 | Oda et al. |
| 2007/0287886 A1 | 12/2007 | Saadat |
| 2007/0287934 A1 | 12/2007 | Babaev |
| 2007/0299425 A1 | 12/2007 | Waner et al. |
| 2008/0004686 A1 | 1/2008 | Hunt et al. |
| 2008/0039715 A1 | 2/2008 | Wilson et al. |
| 2008/0077225 A1 | 3/2008 | Carlin et al. |
| 2008/0082004 A1 | 4/2008 | Banet et al. |
| 2008/0172119 A1 | 7/2008 | Yamasaki et al. |
| 2008/0183128 A1 | 7/2008 | Morriss et al. |
| 2008/0212082 A1 | 9/2008 | Froggatt et al. |
| 2008/0285909 A1 | 11/2008 | Younge et al. |
| 2008/0319290 A1 | 12/2008 | Mao et al. |
| 2009/0054908 A1 | 2/2009 | Zand et al. |
| 2009/0062634 A1 | 3/2009 | Say et al. |
| 2009/0118612 A1 | 5/2009 | Grunwald et al. |
| 2009/0137952 A1 | 5/2009 | Ramamurthy et al. |
| 2009/0234328 A1 | 9/2009 | Cox et al. |
| 2009/0304582 A1 | 12/2009 | Rousso et al. |
| 2009/0314925 A1 | 12/2009 | Van Vorhis et al. |
| 2009/0324161 A1 | 12/2009 | Prisco |
| 2010/0016729 A1 | 1/2010 | Futrell |
| 2010/0030063 A1 | 2/2010 | Lee et al. |
| 2010/0030132 A1 | 2/2010 | Niezgoda et al. |
| 2010/0063534 A1 | 3/2010 | Kugler et al. |
| 2010/0114115 A1 | 5/2010 | Schlesinger et al. |
| 2010/0286531 A1 | 11/2010 | Ryan et al. |
| 2010/0312095 A1 | 12/2010 | Jenkins et al. |
| 2011/0015533 A1 | 1/2011 | Cox et al. |

(56) References Cited

U.S. PATENT DOCUMENTS

| | | | |
|---|---|---|---|
| 2011/0060229 A1* | 3/2011 | Hulvershorn | A61B 5/0215 |
| | | | 600/561 |
| 2011/0090486 A1 | 4/2011 | Udd | |
| 2011/0144481 A1 | 6/2011 | Feer et al. | |
| 2011/0166442 A1 | 7/2011 | Sarvazyan | |
| 2011/0172591 A1 | 7/2011 | Babaev | |
| 2011/0172680 A1 | 7/2011 | Younge et al. | |
| 2011/0237958 A1 | 9/2011 | Onimura | |
| 2011/0242532 A1 | 10/2011 | McKenna | |
| 2011/0245662 A1 | 10/2011 | Eggers et al. | |
| 2011/0288405 A1 | 11/2011 | Razavi et al. | |
| 2011/0295108 A1 | 12/2011 | Cox et al. | |
| 2011/0313280 A1 | 12/2011 | Govari et al. | |
| 2012/0046562 A1 | 2/2012 | Powers et al. | |
| 2012/0065481 A1 | 3/2012 | Hunter et al. | |
| 2012/0101413 A1 | 4/2012 | Beetel et al. | |
| 2012/0136242 A1 | 5/2012 | Qi et al. | |
| 2012/0143029 A1 | 6/2012 | Silverstein et al. | |
| 2012/0184827 A1 | 7/2012 | Shwartz et al. | |
| 2012/0184955 A1 | 7/2012 | Pivotto et al. | |
| 2012/0283747 A1 | 11/2012 | Popovic | |
| 2012/0289783 A1 | 11/2012 | Duindam et al. | |
| 2012/0321243 A1 | 12/2012 | Younge et al. | |
| 2013/0028554 A1 | 1/2013 | Wong et al. | |
| 2013/0072943 A1 | 3/2013 | Parmar | |
| 2013/0090563 A1 | 4/2013 | Weber | |
| 2013/0096482 A1 | 4/2013 | Bertrand et al. | |
| 2013/0104884 A1 | 5/2013 | Vazales et al. | |
| 2013/0188855 A1 | 7/2013 | Desjardins et al. | |
| 2013/0204124 A1 | 8/2013 | Duindam et al. | |
| 2013/0211246 A1 | 8/2013 | Parasher | |
| 2013/0296693 A1 | 11/2013 | Wenzel et al. | |
| 2013/0310668 A1 | 11/2013 | Young | |
| 2013/0317372 A1 | 11/2013 | Eberle et al. | |
| 2013/0324840 A1 | 12/2013 | Zhongping et al. | |
| 2014/0100550 A1 | 4/2014 | Zarei Mahmoodabadi et al. | |
| 2014/0121468 A1 | 5/2014 | Eichenholz | |
| 2014/0206988 A1 | 7/2014 | Ramachandran et al. | |
| 2014/0221829 A1 | 8/2014 | Maitland et al. | |
| 2014/0275997 A1 | 9/2014 | Chopra et al. | |
| 2015/0029511 A1 | 1/2015 | 'T Hooft et al. | |
| 2015/0031987 A1 | 1/2015 | Pameijer et al. | |
| 2015/0080688 A1 | 3/2015 | Cinbis et al. | |
| 2015/0099979 A1 | 4/2015 | Caves et al. | |
| 2015/0119700 A1 | 4/2015 | Liang et al. | |
| 2015/0124264 A1 | 5/2015 | Ramachandran et al. | |
| 2015/0141808 A1 | 5/2015 | Elhawary et al. | |
| 2015/0141854 A1 | 5/2015 | Eberle et al. | |
| 2015/0164571 A1 | 6/2015 | Saadat | |
| 2015/0190221 A1 | 7/2015 | Schaefer et al. | |
| 2015/0209113 A1 | 7/2015 | Burkholz et al. | |
| 2015/0209117 A1 | 7/2015 | Flexman et al. | |
| 2015/0254526 A1 | 9/2015 | Denissen | |
| 2015/0320977 A1 | 11/2015 | Vitullo et al. | |
| 2015/0342665 A1 | 12/2015 | Tiano | |
| 2016/0018602 A1 | 1/2016 | Govari et al. | |
| 2016/0067449 A1 | 3/2016 | Misener et al. | |
| 2016/0102969 A1 | 4/2016 | Verstege et al. | |
| 2016/0166326 A1 | 6/2016 | Bakker et al. | |
| 2016/0166341 A1 | 6/2016 | Iordachita et al. | |
| 2016/0184020 A1 | 6/2016 | Kowalewski et al. | |
| 2016/0213432 A1 | 7/2016 | Flexman et al. | |
| 2016/0220314 A1 | 8/2016 | Huelman et al. | |
| 2016/0256224 A1 | 9/2016 | Wenzel et al. | |
| 2016/0296122 A1 | 10/2016 | Kim et al. | |
| 2016/0331461 A1 | 11/2016 | Cheatham, III et al. | |
| 2016/0349044 A1 | 12/2016 | Marell et al. | |
| 2016/0354038 A1 | 12/2016 | Demirtas et al. | |
| 2017/0020394 A1 | 1/2017 | Harrington | |
| 2017/0065353 A1 | 3/2017 | Ludwin et al. | |
| 2017/0079681 A1 | 3/2017 | Burnside et al. | |
| 2017/0082806 A1 | 3/2017 | Van Der Mark et al. | |
| 2017/0151027 A1 | 6/2017 | Walker et al. | |
| 2017/0173349 A1 | 6/2017 | Pfleiderer et al. | |
| 2017/0196479 A1 | 7/2017 | Liu et al. | |
| 2017/0201036 A1 | 7/2017 | Cohen et al. | |
| 2017/0215973 A1 | 8/2017 | Flexman et al. | |
| 2017/0231699 A1 | 8/2017 | Flexman et al. | |
| 2017/0273542 A1 | 9/2017 | Au | |
| 2017/0273565 A1 | 9/2017 | Ma et al. | |
| 2017/0273628 A1 | 9/2017 | Ofek et al. | |
| 2017/0290563 A1 | 10/2017 | Cole et al. | |
| 2017/0311901 A1 | 11/2017 | Zhao et al. | |
| 2017/0319279 A1 | 11/2017 | Fish et al. | |
| 2018/0008443 A1 | 1/2018 | Cole et al. | |
| 2018/0031493 A1 | 2/2018 | Tojo et al. | |
| 2018/0095231 A1 | 4/2018 | Lowell et al. | |
| 2018/0113038 A1 | 4/2018 | Janabi-Sharifi et al. | |
| 2018/0116551 A1 | 5/2018 | Newman et al. | |
| 2018/0139392 A1 | 5/2018 | Rauniyar et al. | |
| 2018/0140170 A1 | 5/2018 | Van Putten et al. | |
| 2018/0235709 A1 | 8/2018 | Donhowe et al. | |
| 2018/0239124 A1 | 8/2018 | Naruse et al. | |
| 2018/0240237 A1 | 8/2018 | Donhowe et al. | |
| 2018/0250088 A1 | 9/2018 | Brennan et al. | |
| 2018/0264227 A1 | 9/2018 | Flexman et al. | |
| 2018/0279909 A1 | 10/2018 | Noonan et al. | |
| 2018/0289390 A1 | 10/2018 | Amorizzo et al. | |
| 2018/0289927 A1 | 10/2018 | Messerly | |
| 2018/0339134 A1 | 11/2018 | Leo | |
| 2018/0360545 A1 | 12/2018 | Cole et al. | |
| 2019/0059743 A1 | 2/2019 | Ramachandran et al. | |
| 2019/0060003 A1 | 2/2019 | Tuason | |
| 2019/0110844 A1 | 4/2019 | Misener et al. | |
| 2019/0231272 A1 | 8/2019 | Yamaji | |
| 2019/0237902 A1 | 8/2019 | Thompson et al. | |
| 2019/0247132 A1 | 8/2019 | Harks et al. | |
| 2019/0307331 A1 | 10/2019 | Saadat et al. | |
| 2019/0321110 A1 | 10/2019 | Grunwald et al. | |
| 2019/0343424 A1 | 11/2019 | Blumenkranz et al. | |
| 2019/0343702 A1 | 11/2019 | Smith | |
| 2019/0357875 A1 | 11/2019 | Qi et al. | |
| 2019/0365199 A1 | 12/2019 | Zhao et al. | |
| 2019/0374130 A1 | 12/2019 | Bydlon et al. | |
| 2020/0000526 A1 | 1/2020 | Zhao | |
| 2020/0022587 A1 | 1/2020 | Glover et al. | |
| 2020/0022764 A1 | 1/2020 | Flexman et al. | |
| 2020/0030575 A1* | 1/2020 | Bogusky | A61M 16/0488 |
| 2020/0046434 A1 | 2/2020 | Graetzel et al. | |
| 2020/0054399 A1 | 2/2020 | Duindam et al. | |
| 2020/0121482 A1 | 4/2020 | Spector et al. | |
| 2020/0129318 A1 | 4/2020 | Duval et al. | |
| 2020/0188036 A1 | 6/2020 | Ding et al. | |
| 2020/0297442 A1 | 9/2020 | Adebar et al. | |
| 2020/0305983 A1 | 10/2020 | Yampolsky et al. | |
| 2020/0315770 A1 | 10/2020 | Dupont et al. | |
| 2020/0394789 A1 | 12/2020 | Freund et al. | |
| 2021/0015470 A1 | 1/2021 | Prisco et al. | |
| 2021/0023341 A1 | 1/2021 | Decheek et al. | |
| 2021/0030480 A1 | 2/2021 | McMichael et al. | |
| 2021/0045814 A1 | 2/2021 | Thompson et al. | |
| 2021/0068911 A1 | 3/2021 | Walker et al. | |
| 2021/0100627 A1 | 4/2021 | Soper et al. | |
| 2021/0244311 A1 | 8/2021 | Zhao et al. | |
| 2021/0268229 A1 | 9/2021 | Sowards et al. | |
| 2021/0271035 A1 | 9/2021 | Sowards et al. | |
| 2021/0275256 A1 | 9/2021 | Sowards et al. | |
| 2021/0275257 A1 | 9/2021 | Prior et al. | |
| 2021/0282867 A1 | 9/2021 | Tegg et al. | |
| 2021/0298680 A1 | 9/2021 | Sowards et al. | |
| 2021/0330399 A1 | 10/2021 | Netravali et al. | |
| 2021/0401456 A1 | 12/2021 | Cox et al. | |
| 2021/0401509 A1 | 12/2021 | Misener et al. | |
| 2021/0402144 A1 | 12/2021 | Messerly | |
| 2022/0011192 A1 | 1/2022 | Misener et al. | |
| 2022/0034733 A1 | 2/2022 | Misener et al. | |
| 2022/0079683 A1 | 3/2022 | Bydlon et al. | |
| 2022/0096796 A1 | 3/2022 | Mclaughlin et al. | |
| 2022/0110508 A1 | 4/2022 | Van Roosbroeck et al. | |
| 2022/0110695 A1 | 4/2022 | Sowards et al. | |
| 2022/0151568 A1 | 5/2022 | Yao et al. | |
| 2022/0152349 A1 | 5/2022 | Sowards et al. | |
| 2022/0160209 A1 | 5/2022 | Sowards et al. | |
| 2022/0172354 A1 | 6/2022 | Misener et al. | |

(56) References Cited

U.S. PATENT DOCUMENTS

| | | |
|---|---|---|
| 2022/0211442 A1 | 7/2022 | McLaughlin et al. |
| 2022/0233246 A1 | 7/2022 | Misener et al. |
| 2022/0354380 A1 | 11/2022 | Tata et al. |
| 2022/0369934 A1 | 11/2022 | Sowards et al. |
| 2023/0081198 A1 | 3/2023 | Sowards et al. |
| 2023/0097431 A1 | 3/2023 | Sowards et al. |
| 2023/0101030 A1 | 3/2023 | Misener et al. |
| 2023/0108604 A1 | 4/2023 | Messerly et al. |
| 2023/0126813 A1 | 4/2023 | Sowards et al. |
| 2023/0243715 A1 | 8/2023 | Misener et al. |
| 2023/0248444 A1 | 8/2023 | Misener et al. |
| 2023/0251150 A1 | 8/2023 | Misener et al. |
| 2023/0337985 A1 | 10/2023 | Sowards et al. |
| 2023/0346479 A1 | 11/2023 | Muller et al. |
| 2023/0414112 A1 | 12/2023 | Misener et al. |
| 2024/0000515 A1 | 1/2024 | Misener et al. |
| 2024/0050708 A1 | 2/2024 | Misener |
| 2024/0099659 A1 | 3/2024 | Sowards et al. |
| 2024/0108856 A1 | 4/2024 | Messerly |
| 2024/0156383 A1 | 5/2024 | Sawada |
| 2024/0216077 A1 | 7/2024 | Thompson et al. |
| 2024/0335237 A1 | 10/2024 | Sowards et al. |
| 2024/0353275 A1 | 10/2024 | Misener et al. |
| 2024/0383133 A1 | 11/2024 | Bydlon et al. |
| 2025/0020453 A1 | 1/2025 | Thompson et al. |
| 2025/0060266 A1 | 2/2025 | Messerly |
| 2025/0186135 A1 | 6/2025 | McLaughlin et al. |
| 2025/0224304 A1 | 7/2025 | Misener et al. |
| 2025/0325193 A1 | 10/2025 | Misener et al. |
| 2025/0375249 A1 | 12/2025 | Misener et al. |
| 2025/0387598 A1 | 12/2025 | Messerly |
| 2026/0013952 A1 | 1/2026 | Sowards et al. |
| 2026/0047765 A1 | 2/2026 | Misener et al. |

FOREIGN PATENT DOCUMENTS

| | | |
|---|---|---|
| CN | 113080937 A | 7/2021 |
| DE | 102016109601 A1 | 11/2017 |
| EP | 2240111 A2 | 10/2010 |
| EP | 2907445 A1 | 8/2015 |
| EP | 3545849 A1 | 10/2019 |
| EP | 3705020 A1 | 9/2020 |
| JP | 7366562 B2 | 10/2023 |
| KR | 20190098512 A | 8/2019 |
| WO | 9964099 A1 | 12/1999 |
| WO | 2006113394 A2 | 10/2006 |
| WO | 2006122001 A2 | 11/2006 |
| WO | 2007002323 A2 | 1/2007 |
| WO | 2009155325 A2 | 12/2009 |
| WO | 2011121516 A2 | 10/2011 |
| WO | 2011141830 A1 | 11/2011 |
| WO | 2011150376 A1 | 12/2011 |
| WO | 2012064769 A2 | 5/2012 |
| WO | 2015044930 A1 | 4/2015 |
| WO | 2015074045 A2 | 5/2015 |
| WO | 2016038492 A1 | 3/2016 |
| WO | 2016051302 A1 | 4/2016 |
| WO | 2016061431 A1 | 4/2016 |
| WO | 2016149819 A1 | 9/2016 |
| WO | 2018096491 A1 | 5/2018 |
| WO | 2019037071 A1 | 2/2019 |
| WO | 2019046769 A1 | 3/2019 |
| WO | 2019070423 A1 | 4/2019 |
| WO | 2019230713 A1 | 12/2019 |
| WO | 2020182997 A1 | 9/2020 |
| WO | 2021030092 A1 | 2/2021 |
| WO | 2021108688 A1 | 6/2021 |
| WO | 2021108697 A1 | 6/2021 |
| WO | 2021138096 A1 | 7/2021 |
| WO | 2021216089 A1 | 10/2021 |
| WO | 2022031613 A1 | 2/2022 |
| WO | 2022081723 A1 | 4/2022 |
| WO | 2022150411 A1 | 7/2022 |
| WO | 2022164902 A1 | 8/2022 |
| WO | 2022245987 A1 | 11/2022 |
| WO | 2023043954 A1 | 3/2023 |
| WO | 2023049443 A1 | 3/2023 |
| WO | 2023055810 A1 | 4/2023 |
| WO | 2023076143 A1 | 5/2023 |
| WO | 2023211752 A1 | 11/2023 |
| WO | 2024006384 A1 | 1/2024 |
| WO | 2024006441 A1 | 1/2024 |
| WO | 2024015464 A1 | 1/2024 |
| WO | 2024064334 A1 | 3/2024 |
| WO | 2024215665 A1 | 10/2024 |

OTHER PUBLICATIONS

U.S. Appl. No. 17/500,678, filed Oct. 13, 2021 Advisory Action dated Nov. 6, 2024.

U.S. Appl. No. 17/500,678, filed Oct. 13, 2021 Final Office Action dated Aug. 27, 2024.

U.S. Appl. No. 17/569,350, filed Jan. 5, 2022 Notice of Allowance dated Nov. 7, 2024.

U.S. Appl. No. 17/728,802, filed Apr. 25, 2022 Non-Final Office Action dated Aug. 28, 2024.

U.S. Appl. No. 17/852,138, filed Jun. 28, 2022 Non-Final Office Action dated Sep. 18, 2024.

U.S. Appl. No. 17/853,590, filed Jun. 29, 2022 Non-Final Office Action dated Oct. 17, 2024.

U.S. Appl. No. 17/955,019, filed Sep. 28, 2022 Non-Final Office Action dated Sep. 27, 2024.

U.S. Appl. No. 18/132,623, filed Apr. 10, 2023, Final Office Action dated Sep. 6, 2024.

U.S. Appl. No. 18/607,144, filed Mar. 15, 2024 Non-Final Office Action dated Sep. 24, 2024.

Ogawa, K.; Koyama, S.; Ishizawa, H.; Fujiwara, S.; Fujimoto, K. Simultaneous Measurement of Heart Sound, PulseWave and Respiration with Single Fiber Bragg Grating Sensor. In Proceedings of the 2018 IEEE International Symposium on Medical Measurements and Applications (MeMeA), Rome, Italy, Jun. 11-13, 2018.

U.S. Appl. No. 17/500,678, filed Oct. 13, 2021 Final Office Action dated Jun. 11, 2025.

U.S. Appl. No. 17/585,219, filed Jan. 26, 2022 Notice of Allowance dated Jun. 17, 2025.

U.S. Appl. No. 17/728,802, filed Apr. 25, 2022 Non-Final Office Action dated May 19, 2025.

U.S. Appl. No. 17/952,645, filed Sep. 26, 2022 Final Office Action dated Jul. 14, 2025.

U.S. Appl. No. 17/971,873, filed Oct. 24, 2022 Notice of Allowance dated Jun. 6, 2025.

U.S. Appl. No. 18/132,891, filed Apr. 10, 2023 Restriction Requirement dated Jun. 2, 2025.

U.S. Appl. No. 18/761,248, filed Jul. 1, 2024 Non-Final Office Action dated Aug. 6, 2025.

U.S. Appl. No. 17/585,219, filed Jan. 26, 2022 Non-Final Office Action dated Feb. 27, 2025.

U.S. Appl. No. 17/728,802, filed Apr. 25, 2022 Advisory Action dated Apr. 4, 2025.

U.S. Appl. No. 17/747,903, filed May 18, 2022 Advisory Action dated Apr. 22, 2025.

U.S. Appl. No. 17/853,590, filed Jun. 29, 2022 Notice of Allowance dated Mar. 5, 2025.

U.S. Appl. No. 17/952,645, filed Sep. 26, 2022 Non-Final Office Action dated Feb. 28, 2025.

U.S. Appl. No. 17/955,019, filed Sep. 28, 2022 Advisory Action dated Apr. 16, 2025.

U.S. Appl. No. 18/132,231, filed Apr. 7, 2023 Notice of Allowance dated Apr. 10, 2025.

U.S. Appl. No. 18/383,809, filed Oct. 25, 2023 Notice of Allowance dated Apr. 30, 2025.

U.S. Appl. No. 18/538,111, filed Dec. 13, 2023 Notice of Allowance dated Apr. 23, 2025.

U.S. Appl. No. 18/607,144, filed Mar. 15, 2024 Final Office Action dated Feb. 19, 2025.

U.S. Appl. No. 18/607,144, filed Mar. 15, 2024 Notice of Allowance dated Apr. 5, 2025.

(56) References Cited

OTHER PUBLICATIONS

Dziuda L et al: "Monitoring Respiration and Cardiac Activity Using Fiber Bragg Grating-Based Sensor", IEEE Transactions on Biomedical Engineering vol. 59, No. 7, Jul. 2012 pp. 1934-1942.

Dziuda L. et al: "Fiber-optic sensor for monitoring respiration and cardiac activity", 2011 IEEE Sensors Proceedings : Limerick, Ireland, Oct. 2011 pp. 413-416.

EP 20853352.1 filed Mar. 7, 2022 Extended European Search Report dated Jul. 27, 2023.

EP 20893677.3 filed Jun. 22, 2022 Extended European Search Report dated Oct. 13, 2023.

EP 20894633.5 filed Jun. 22, 2022 Extended European Search Report dated Oct. 16, 2023.

Fiber Optic RealShape (FORS) technology—research. Philips. (Oct. 18, 2018). Retrieved Feb. 28, 2023, from https:// www.philips.com/a-w/research/research-programs/fors.html (Year: 2018).

Jackle Sonja et al. "Three-dimensional guidance including shape sensing of a stentgraft system for endovascular aneurysm repair." International Journal of Computer Assisted Radiology and Surgery, Springer DE. vol. 15, No. 6, May 7, 2020.

PCT/US2018/026493 filed Apr. 6, 2018 International Search Report and Written Opinion dated Jun. 22, 2018.

PCT/US2020/044801 filed Aug. 3, 2020 International Search Report and Written Opinion dated Oct. 26, 2020.

PCT/US2020/062396 filed Nov. 25, 2020 International Preliminary Report on Patentability dated Jan. 29, 2021.

PCT/US2020/062396 filed Nov. 25, 2020 International Search Report and Written Opinion dated Mar. 2, 2021.

PCT/US2020/062407 filed Nov. 25, 2020 International Preliminary Report on Patentability dated Jan. 25, 2021.

PCT/US2020/062407 filed Nov. 25, 2020 International Search Report and Written Opinion dated Mar. 11, 2021.

PCT/US2021/038899 filed Jun. 24, 2021 International Search Report and Written Opinion dated Oct. 6, 2021.

PCT/US2021/038954 filed Jun. 24, 2021 International Search Report and Written Opinion dated Oct. 28, 2021.

PCT/US2021/041128 filed Jul. 9, 2021 International Search Report and Written Opinion dated Oct. 25, 2021.

PCT/US2021/044216 filed Aug. 2, 2021 International Search Report and Written Opinion dated Nov. 18, 2021.

PCT/US2021/052046 filed Sep. 24, 2021 International Search Report and Written Opinion dated Jan. 11, 2022.

PCT/US2021/054802 filed Oct. 13, 2021 International Search Report and Written Opinion dated Feb. 2, 2022.

PCT/US2022/011347 filed Jan. 5, 2022 International Search Report and Written Opinion dated May 3, 2022.

PCT/US2022/013897 filed Jan. 26, 2022 International Search Report and Written Opinion dated May 11, 2022.

PCT/US2022/029894 filed May 18, 2022, International Search Report and Written Opinion dated Sep. 1, 2022.

PCT/US2022/043706 filed Sep. 16, 2022 International Search Report and Written Opinion dated Nov. 24, 2022.

PCT/US2022/044696 filed Sep. 26, 2022 International Search Report and Written Opinion dated Jan. 23, 2023.

PCT/US2022/045051 filed Sep. 28, 2022 International Search Report and Written Opinion dated Jan. 2, 2023.

PCT/US2022/047538 filed Oct. 24, 2022 International Search Report and Written Opinion dated Jan. 26, 2023.

PCT/US2023/019239 filed Apr. 20, 2023 International Search Report and Written Opinion dated Jul. 20, 2023.

PCT/US2023/026487 filed Jun. 28, 2023 International Search Report and Written Opinion dated Sep. 6, 2023.

PCT/US2023/026581 filed Jun. 29, 2023 International Search Report and Written Opinion dated Oct. 27, 2023.

PCT/US2023/033471 filed Sep. 22, 2023 International Search Report and Written Opinion dated Dec. 21, 2023.

U.S. Appl. No. 15/947,267, filed Apr. 6, 2018 Examiner's Answer dated Novemeber 28, 2022.

U.S. Appl. No. 15/947,267, filed Apr. 6, 2018 Final Office Action dated Apr. 22, 2022.

U.S. Appl. No. 15/947,267, filed Apr. 6, 2018 Notice of Allowance dated Jul. 16, 2024.

U.S. Appl. No. 16/984,104, filed Aug. 3, 2020 Final Office Action dated Sep. 21, 2023.

U.S. Appl. No. 16/984,104, filed Aug. 3, 2020 Non-Final Office Action dated Jun. 22, 2023.

U.S. Appl. No. 16/984,104, filed Aug. 3, 2020 Notice of Allowance dated Nov. 21, 2023.

U.S. Appl. No. 16/984,104, filed Aug. 3, 2020 Restriction Requirement dated Mar. 13, 2023.

U.S. Appl. No. 17/105,259, filed Nov. 25, 2020, Notice of Allowance dated Jul. 20, 2022.

U.S. Appl. No. 17/105,310, filed Nov. 25, 2020 Non-Final Office Action dated Feb. 22, 2023.

U.S. Appl. No. 17/105,310, filed Nov. 25, 2020 Notice of Allowance dated Aug. 2, 2023.

U.S. Appl. No. 17/357,186, filed Jun. 24, 2021 Non Final Office Action dated May 30, 2023.

U.S. Appl. No. 17/357,186, filed Jun. 24, 2021 Notice of Allowance dated Aug. 23, 2023.

U.S. Appl. No. 17/357,186, filed Jun. 24, 2021 Restriction Requirement dated Mar. 7, 2023.

U.S. Appl. No. 17/357,561, filed Jun. 24, 2021 Non-Final Office Action dated Aug. 11, 2022.

U.S. Appl. No. 17/357,561, filed Jun. 24, 2021 Notice of Allowance dated Dec. 9, 2022.

U.S. Appl. No. 17/371,993, filed Jul. 9, 2021 Non-Final Office Action dated Jul. 12, 2022.

U.S. Appl. No. 17/371,993, filed Jul. 9, 2021 Notice of Allowance dated Nov. 3, 2022.

U.S. Appl. No. 17/392,002, filed Aug. 2, 2021, Corrected Notice of Allowability dated Feb. 23, 2023.

U.S. Appl. No. 17/392,002, filed Aug. 2, 2021, Non-Final Office Action dated Sep. 12, 2022.

U.S. Appl. No. 17/392,002, filed Aug. 2, 2021, Notice of Allowance dated Jan. 19, 2023.

P.J. de Feyter, P. Kay, C. Disco, P.W. Serruys, "Reference chart derived from post-stent-implantation intravascular ultrasound predictors of 6-month expected restenosis on quantitative coronary angiography." Circulation. vol. 100, No. 17 (Year: 1999).

PCT/US2023/026581 filed Jun. 29, 2023 International Preliminary Report on Patentability dated Dec. 18, 2024.

U.S. Appl. No. 17/500,678, filed Oct. 13, 2021 Non-Final Office Action dated Dec. 4, 2024.

U.S. Appl. No. 17/585,219, filed Jan. 26, 2022 Restriction Requirement dated Dec. 2, 2024.

U.S. Appl. No. 17/728,802, filed Apr. 25, 2022 Final Office Action dated Jan. 17, 2025.

U.S. Appl. No. 17/747,903, filed May 18, 2022 Final Office Action dated Jan. 27, 2025.

U.S. Appl. No. 17/852,138, filed Jun. 28, 2022 Notice of Allowance dated Feb. 12, 2025.

U.S. Appl. No. 17/955,019, filed Sep. 28, 2022 Final Office Action dated Feb. 4, 2025.

U.S. Appl. No. 17/971,873, filed Oct. 24, 2022 Non-Final Office Action dated Dec. 27, 2024.

U.S. Appl. No. 18/132,231, filed Apr. 7, 2023 Final Office Action dated Jan. 31, 2025.

U.S. Appl. No. 18/132,623, filed Apr. 10, 2023, Notice of Allowance dated Nov. 19, 2024.

U.S. Appl. No. 18/383,809, filed Oct. 25, 2023 Non-Final Office Action dated Dec. 16, 2024.

U.S. Appl. No. 18/538,111, filed Dec. 13, 2023 Final Office Action dated Feb. 4, 2025.

U.S. Appl. No. 17/484,960, filed Sep. 24, 2021 Non-Final Office Action dated Oct. 5, 2023.

U.S. Appl. No. 17/484,960, filed Sep. 24, 2021 Notice of Allowance dated Apr. 12, 2024.

U.S. Appl. No. 17/500,678, filed Oct. 13, 2021 Advisory Action dated Dec. 7, 2023.

U.S. Appl. No. 17/500,678, filed Oct. 13, 2021 Final Office Action dated Sep. 21, 2023.

(56) References Cited

OTHER PUBLICATIONS

U.S. Appl. No. 17/500,678, filed Oct. 13, 2021 Non-Final Office Action dated Jan. 19, 2024.

U.S. Appl. No. 17/500,678, filed Oct. 13, 2021 Non-Final Office Action dated Mar. 15, 2023.

U.S. Appl. No. 17/569,350, filed Jan. 5, 2022 Advisory Action dated Jul. 12, 2024.

U.S. Appl. No. 17/569,350, filed Jan. 5, 2022 Final Office Action dated Apr. 23, 2024.

U.S. Appl. No. 17/747,903, filed May 18, 2022 Non-Final Office Action dated Aug. 15, 2024.

U.S. Appl. No. 17/747,903, filed May 18, 2022 Restriction Requirement dated May 28, 2024.

U.S. Appl. No. 17/955,019, filed Sep. 28, 2022 Restriction Requirement dated Jun. 6, 2024.

U.S. Appl. No. 18/079,653, filed Dec. 12, 2022 Non-Final Office Action dated Feb. 6, 2024.

U.S. Appl. No. 18/079,653, filed Dec. 12, 2022 Notice of Allowance dated Jun. 4, 2024.

U.S. Appl. No. 18/132,231, filed Apr. 7, 2023 Non-Final Office Action dated Jul. 12, 2024.

U.S. Appl. No. 18/132,623, filed Apr. 10, 2023, Non-Final Office Action dated May 3, 2024.

U.S. Appl. No. 18/135,337, filed Apr. 17, 2023 Non-Final Office Action dated Dec. 22, 2023.

U.S. Appl. No. 18/135,337, filed Apr. 17, 2023 Notice of Allowance dated Mar. 8, 2024.

U.S. Appl. No. 18/538,111, filed Dec. 13, 2023 Non-Final Office Action dated Aug. 9, 2024.

U.S. Appl. No. 15/947,267, filed Apr. 6, 2018 Final Office Action dated Jun. 30, 2021.

U.S. Appl. No. 15/947,267, filed Apr. 6, 2018 Final Office Action dated Nov. 10, 2020.

U.S. Appl. No. 15/947,267, filed Apr. 6, 2018 Non-Final Office Action dated Mar. 12, 2021.

U.S. Appl. No. 15/947,267, filed Apr. 6, 2018 Non-Final Office Action dated May 29, 2020.

U.S. Appl. No. 15/947,267, filed Apr. 6, 2018 Non-Final Office Action dated Oct. 13, 2021.

U.S. Appl. No. 17/569,350, filed Jan. 5, 2022 Non-Final Office Action dated Aug. 12, 2024.

U.S. Appl. No. 17/569,350, filed Jan. 5, 2022 Non-Final Office Action dated Jan. 8, 2024.

U.S. Appl. No. 17/971,873, filed Oct. 24, 2022 Non-Final Office Action dated Jun. 6, 2024.

Karagiannis Martha JP et al: "Effects of oral intake of water in patients with oropharyngeal dysphagia", BMC Geriatrics, Biomed Central Ltd London, GB, vol. 11, No. 1, Mar. 1, 2011 (Mar. 1, 2011), p. 9, XP021086906, ISSN; 1471-2318, DOI; 10.1186/1471-2318-11-9 p. 5: chapter "Lung related complications".

PCT/US2025/042084 filed Aug. 14, 2025 International Search Report and Written Opinion dated Nov. 24, 2025.

U.S. Appl. No. 17/500,678, filed Oct. 13, 2021 Notice of Allowance dated Sep. 30, 2025.

U.S. Appl. No. 17/728,802, filed Apr. 25, 2022 Final Office Action dated Nov. 21, 2025.

U.S. Appl. No. 17/747,903, filed May 18, 2022 Notice of Allowance dated Sep. 9, 2025.

U.S. Appl. No. 17/952,645, filed Sep. 26, 2022 Non-Final Office Action dated Nov. 12, 2025.

U.S. Appl. No. 17/955,019, filed Sep. 28, 2022 Non-Final Office Action dated Aug. 21, 2025.

U.S. Appl. No. 18/132,891, filed Apr. 10, 2023 Non-Final Office Action dated Aug. 20, 2025.

U.S. Appl. No. 18/371,629, filed Sep. 22, 2023 Non-Final Office Action dated Sep. 22, 2025.

U.S. Appl. No. 18/761,248, filed Jul. 1, 2024 Notice of Allowance dated Nov. 21, 2025.

U.S. Appl. No. 18/936,320, filed Nov. 4, 2024 Non-Final Office Action dated Sep. 18, 2025.

U.S. Appl. No. 17/728,802, filed Apr. 25, 2022 Advisory Action dated Feb. 17, 2026.

U.S. Appl. No. 17/945,934, filed Sep. 15, 2022 Non-Final Office Action dated Jan. 29, 2026.

U.S. Appl. No. 17/955,019, filed Sep. 28, 2022 Final Office Action dated Mar. 6, 2026.

U.S. Appl. No. 18/132,891, filed Apr. 10, 2023 Final Office Action dated Jan. 14, 2026.

U.S. Appl. No. 18/371,629, filed Sep. 22, 2023 Advisory Action dated Mar. 19, 2026.

U.S. Appl. No. 18/371,629, filed Sep. 22, 2023 Final Office Action dated Jan. 9, 2026.

U.S. Appl. No. 18/808,868, filed Aug. 19, 2024 Restriction Requirement dated Feb. 18, 2026.

U.S. Appl. No. 18/936,320, filed Nov. 4, 2024 Advisory Action dated Mar. 27, 2026.

U.S. Appl. No. 18/936,320, filed Nov. 4, 2024 Final Office Action dated Jan. 22, 2026.

U.S. Appl. No. 19/058,347, filed Feb. 20, 2025 Non-Final Office Action dated Mar. 26, 2026.

* cited by examiner

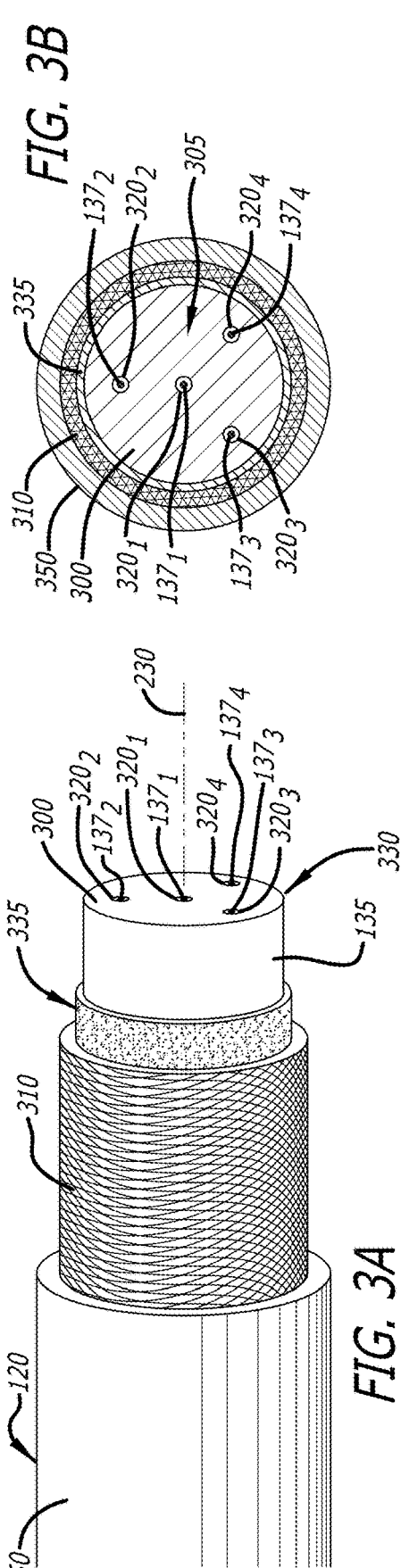
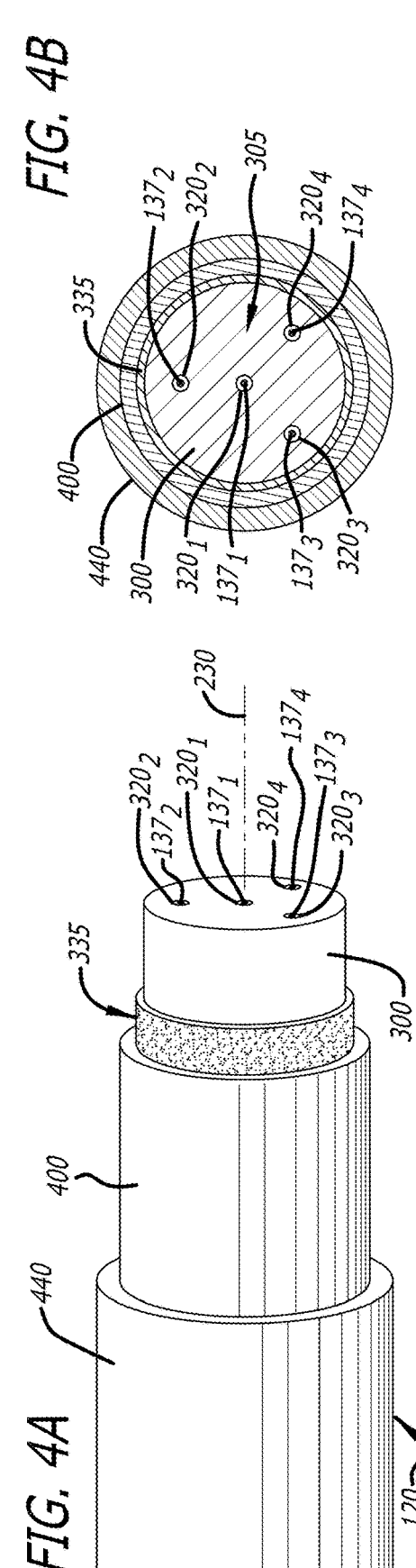

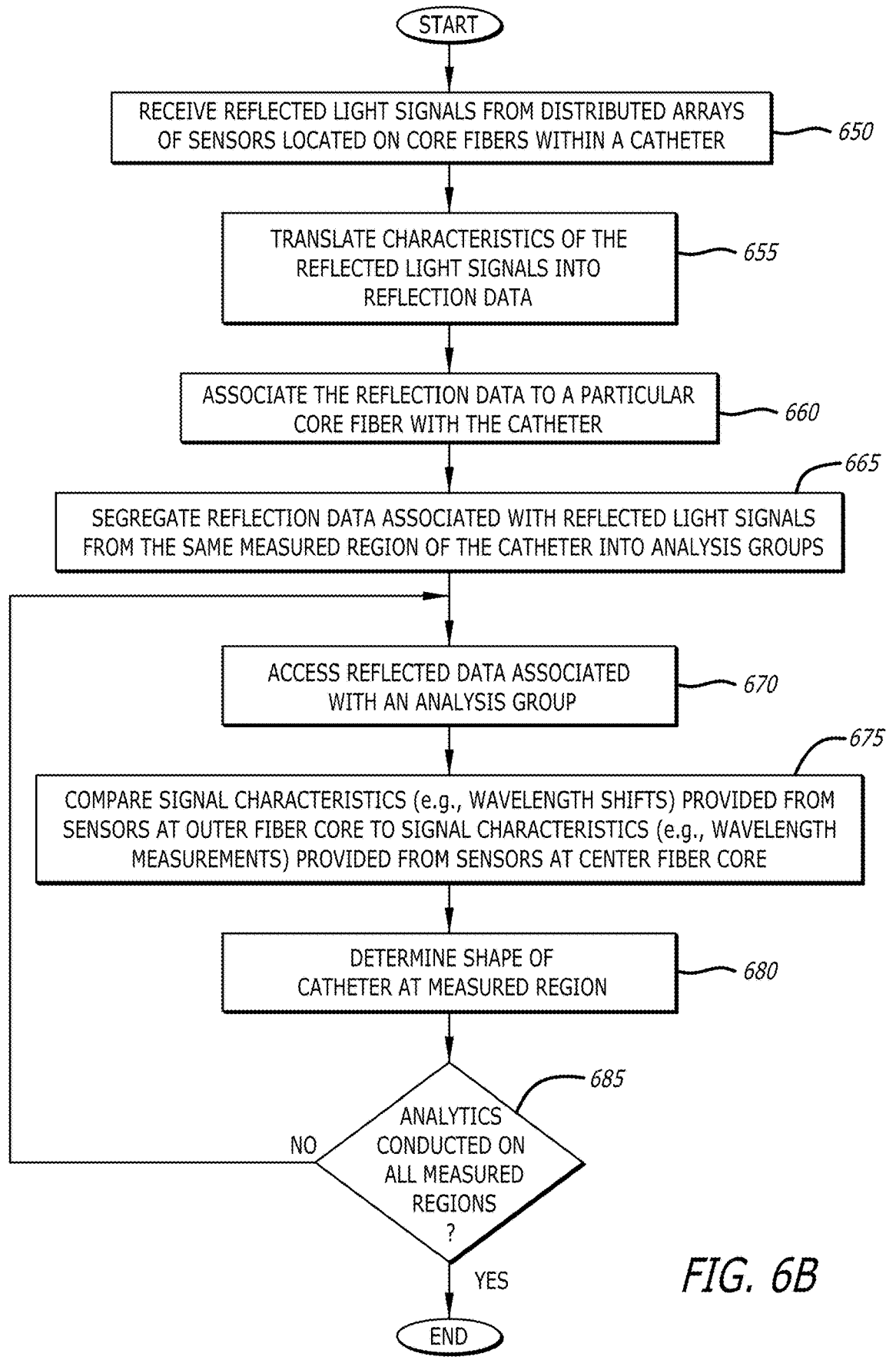

START

RECEIVE REFLECTED LIGHT SIGNALS FROM DISTRIBUTED ARRAYS OF SENSORS LOCATED ON CORE FIBERS WITHIN A CATHETER ⟋ 650

TRANSLATE CHARACTERISTICS OF THE REFLECTED LIGHT SIGNALS INTO REFLECTION DATA ⟋ 655

ASSOCIATE THE REFLECTION DATA TO A PARTICULAR CORE FIBER WITH THE CATHETER ⟋ 660

SEGREGATE REFLECTION DATA ASSOCIATED WITH REFLECTED LIGHT SIGNALS FROM THE SAME MEASURED REGION OF THE CATHETER INTO ANALYSIS GROUPS ⟋ 665

ACCESS REFLECTED DATA ASSOCIATED WITH AN ANALYSIS GROUP ⟋ 670

COMPARE SIGNAL CHARACTERISTICS (e.g., WAVELENGTH SHIFTS) PROVIDED FROM SENSORS AT OUTER FIBER CORE TO SIGNAL CHARACTERISTICS (e.g., WAVELENGTH MEASUREMENTS) PROVIDED FROM SENSORS AT CENTER FIBER CORE ⟋ 675

DETERMINE SHAPE OF CATHETER AT MEASURED REGION ⟋ 680

ANALYTICS CONDUCTED ON ALL MEASURED REGIONS ? ⟋ 685

NO

YES

END

FIG. 6B

FIBER OPTICS OXIMETRY SYSTEM FOR DETECTION AND CONFIRMATION

PRIORITY

This application is a continuation of U.S. patent application Ser. No. 17/484,960, filed Sep. 24, 2021, now U.S. Pat. No. 12,064,569, which claims the benefit of priority to U.S. Provisional Application No. 63/083,457, filed Sep. 25, 2020, which is incorporated by reference in its entirety into this application.

BACKGROUND

In the past, certain intravascular guidance of medical devices, such as guidewires and catheters for example, have used fluoroscopic methods for tracking tips of the medical devices and determining whether distal tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

More recently, electromagnetic tracking systems have been used involving stylets. Generally, electromagnetic tracking systems feature three components: a field generator, a sensor unit and control unit. The field generator uses several coils to generate a position-varying magnetic field, which is used to establish a coordinate space. Attached to the stylet, such as near a distal end (tip) of the stylet for example, the sensor unit includes small coils in which current is induced via the magnetic field. Based on the electrical properties of each coil, the position and orientation of the medical device may be determined within the coordinate space. The control unit controls the field generator and captures data from the sensor unit.

Although electromagnetic tracking systems avoid line-of-sight reliance in tracking the tip of a stylet while obviating radiation exposure and potentially harmful contrast media associated with fluoroscopic methods, electromagnetic tracking systems are prone to interference. More specifically, since electromagnetic tracking systems depend on the measurement of magnetic fields produced by the field generator, these systems are subject to electromagnetic field interference, which may be caused by the presence of many different types of consumer electronics such as cellular telephones. Additionally, electromagnetic tracking systems are subject to signal drop out, depend on an external sensor, and are defined to a limited depth range.

Disclosed herein is a system including a medical instrument having disposed therein an optical fiber and methods performed thereby where the system is configured to provide confirmation of tip placement or tracking information using optical fiber technology. Further, the system is configured to detect oxygen levels of blood within a vasculature of a patient. Some embodiments combine the oxygen level detection functionality with one or more of a fiber optic shape sensing functionality, intravascular electrocardiogram (ECG) monitoring, impedance/conductance sensing and blood flow directional detection.

SUMMARY

Briefly summarized, embodiments disclosed herein are directed to systems, apparatus and methods for obtaining oximetry data (such as oxygen level) and, optionally, three-dimensional (3D) information (reflected light) correspond-ing to a trajectory and/or shape of a medical instrument, such as a catheter, a guidewire, or a stylet, via a fiber optic core during advancement through a vasculature of a patient, and assisting in navigation of the medical instrument during advancement.

More particularly, in some embodiments, the medical instrument includes one or more optical fiber cores, where each are configured with an array of sensors (reflective gratings), which are spatially distributed over a prescribed length of the core fiber to generally sense external strain and temperature on those regions of the core fiber occupied by the sensor. Each optical fiber core is configured to receive light (e.g., broadband light, infrared light, near infrared light, etc.) from a console during advancement through the vasculature of a patient, where the light propagates along at least a partial distance of the optical fiber core toward the distal end. For purposes of clarity, the terms incident light or broadband incident light may be utilized in the description below; however, infrared light and near infrared light may be alternatively utilized. Given that each sensor positioned along the optical fiber core is configured to reflect light of a different, specific spectral width, the array of sensors enables distributed measurements throughout the prescribed length of the medical instrument. These distributed measurements may include wavelength shifts having a correlation with strain and/or temperature experienced by the sensor.

The reflected light from the sensors (reflective gratings) within an optical fiber core is returned from the medical instrument for processing by the console. The physical state of the medical instrument may be ascertained based on analytics of the wavelength shifts of the reflected light. For example, the strain caused through bending of the medical instrument and hence angular modification of the optical fiber core, causes different degrees of deformation. The different degrees of deformation alter the shape of the sensors (reflective grating) positioned on the optical fiber core, which may cause variations (shifts) in the wavelength of the reflected light from the sensors positioned on the optical fiber core. The optical fiber core may comprise a single optical fiber, or a plurality of optical fibers (in which case, the optical fiber core is referred to as a "multi-core optical fiber").

As used herein, the term "core fiber," generally refers to a single optical fiber core disposed within a medical device. Thus, discussion of a core fiber refers to single optical fiber core and discussion of a multi-core optical fiber refers to a plurality of core fibers. Various embodiments discussed below to detection of the health (and particularly the damage) that occurs in each of an optical fiber core of medical instrument including (i) a single core fiber, and (ii) a plurality of core fibers. It is noted that in addition to strain altering the shape of a sensor, ambient temperature variations may also alter the shape of a sensor, thereby causing variations (shifts) in the wavelength of the reflected light from the sensors positioned on the optical fiber core.

More specifically, the optical fiber disposed within the medical instrument may be configured to act as a measurement system of oxygen within vessels or locations within the vasculature to verify placement of a tip of the medical instrument therein. Specifically, a measured oxygen level (also referred to as oxygen level) may indicate a particular location within the vasculature (e.g., a vessel contains a lower volume of blood than the right atrium). As incident light provided by the console propagates to the distal end of the medical instrument, light may be emitted from the distal tip at a particular wavelength that is absorbed by oxygen molecules within the blood. A portion of light is absorbed by oxygen molecules present within each red blood cell, and a portion is reflected by the red blood cells. The reflected portion is received by the distal tip of the optical fiber, and subsequently propagates back to the console. The console is configured to analyze the reflected light from the red blood cells by correlating the reflected light to an oxygen level of the blood proximate the location of the distal tip. More specifically, the reflected light from the red blood cells provides an indication as to an absorption level of the light, which corresponds to an oxygen level. For example, a higher the oxygen level will result in a greater absorption level, which will affect the light reflected from the red blood cells. It should be noted that the absorption by oxygen molecules and reflection of the incident light is not limited or restricted to red bloods cells. For example, tissue and organs within the patient body may also absorb incident light (via oxygen molecules) and reflect incident light.

Stated differently, the absorption of the light by oxygen molecules decreases ("quenches") the light, where the degree of quenching is indicated by the amount of reflected light received by the distal tip of the optical fiber. In other words, absorption of the light (e.g., optical absorption) by oxygen molecules decreases the intensity of the emitted light, where the change in intensity may be measured based on the intensity of the light reflected from the red bloods cells.

The light reflected by the red blood cells is analyzed by logic of the console to determine a location of the distal tip of the optical fiber based on a comparison of the reflected light with data corresponding to known locations with a vasculature as the amount of oxygen within the blood varies depending on its location within the patient's body.

In particular, the reflected light is received by an optical receiver of the console, which is configured to translate the reflected light signals into reflection data, namely data in the form of electrical signals representative of the reflected light signals. The logic of the console is configured to determine a correlation between the reflection data and blood oxygen levels, where the logic may then correlate a blood oxygen level to a particular location of the distal tip of the optical fiber within the vasculature. In some embodiments, the site at which the optical fiber entered the vasculature may be utilized in determining the location within the vasculature. For instance, when two locations each closely correlate to the determined oxygen level, the logic of the console may select a particular location based on proximity to the entry site, and optionally knowledge of advancement of the distal tip of the optical fiber within the vasculature. For example, the logic of the console may select a location option based on oxygen levels based on proximity to the entry site, e.g., a location option within the shoulder may be selected over a location option in the leg when the entry site of the optical fiber is the cephalic vein of a patient's forearm. Other embodiments utilizing the reflection data are discussed below that may also assist a clinician in navigating advancement of the optical fiber (and corresponding medical instrument).

Similarly, blood flow direction may be monitored through analysis of the reflection data. The direction of the flow of blood may affect the amount of light that is reflected from the red blood cells and received by the distal tip of the optical fiber. For example, when the direction of blood flow in is the direction opposite advancement of the optical fiber (e.g., coming toward the distal tip of the optical fiber), a greater level of reflection may be detected as compared to a detected level of reflection when the direction of blood flow is in the same direction as advancement of the optical fiber.

As a result, the intensity of the reflected light lead to a determination as to the direction of the flow of blood.

Specific embodiments of the disclosure include utilization of a medical instrument, such as a stylet, featuring a multi-core optical fiber and a conductive medium that collectively operate for tracking placement with a body of a patient of the stylet or another medical device (such as a catheter) in which the stylet is disposed. In lieu of a stylet, a guidewire may be utilized. For convenience, embodiments are generally discussed where the optical fiber core is disposed within a stylet; however, the disclosure is not intended to be so limited as the functionality involving detection of the health of an optical fiber core disclosed herein may be implemented regardless of the medical device in which the optical fiber core is disposed. In some embodiments, the optical fiber core may be integrated directly into a wall of the catheter.

In some embodiments, the optical fiber core of a stylet is configured to return information for use in identifying its physical state (e.g., shape length, shape, and/or form) of (i) a portion of the stylet (e.g., tip, segment of stylet, etc.) or a portion of a catheter inclusive of at least a portion of the stylet (e.g., tip, segment of catheter, etc.) or (ii) the entirety or a substantial portion of the stylet or catheter within the body of a patient (hereinafter, described as the "physical state of the stylet" or the "physical state of the catheter"). According to one embodiment of the disclosure, the returned information may be obtained from reflected light signals of different spectral widths, where each reflected light signal corresponds to a portion of broadband incident light propagating along a core of the multi-core optical fiber (core fiber) that is reflected back over the core fiber by a particular sensor located on the core fiber. One illustrative example of the returned information may pertain to a change in signal characteristics of the reflected light signal returned from the sensor, where wavelength shift is correlated to (mechanical) strain on the core fiber or a detected change in ambient temperature.

In some embodiments, the core fiber utilizes a plurality of sensors and each sensor is configured to reflect a different spectral range of the incident light (e.g., different light frequency range). Based on the type and degree of strain asserted on each core fiber, the sensors associated with that core fiber may alter (shift) the wavelength of the reflected light to convey the type and degree of stain on that core fiber at those locations of the stylet occupied by the sensors. The sensors are spatially distributed at various locations of the core fiber between a proximal end and a distal end of the stylet so that shape sensing of the stylet may be conducted based on analytics of the wavelength shifts. Herein, the shape sensing functionality is paired with the ability to simultaneously pass an electrical signal through the same member (stylet) through conductive medium included as part of the stylet.

Similarly, the sensors may alter (shift) the wavelength of the reflected light to convey sensed variations in ambient temperature. The alterations in response to detected variations in ambient temperature thereby provide for a temperature sensing functionality.

More specifically, in some embodiments each core fiber of the multi-core optical fiber is configured with an array of sensors, which are spatially distributed over a prescribed length of the core fiber to generally sense external strain on or variations in ambient temperature proximate those regions of the core fiber occupied by the sensor. Given that each sensor positioned along the same core fiber is configured to reflect light of a different, specific spectral width, the array of sensors enables distributed measurements throughout the prescribed length of the multi-core optical fiber. These distributed measurements may include wavelength shifts having a correlation with strain experienced and/or temperature variations detected by the sensor.

In more detail, each sensor may operate as a reflective grating such as a fiber Bragg grating (FBG), namely an intrinsic sensor corresponding to a permanent, periodic refractive index change inscribed into the core fiber. Stated differently, the sensor operates as a light reflective mirror for a specific spectral width (e.g., a specific wavelength or specific range of wavelengths). As a result, as broadband incident light is supplied by an optical light source and propagates through a particular core fiber, upon reaching a first sensor of the distributed array of sensors for that core fiber, light of a prescribed spectral width associated with the first sensor is reflected back to an optical receiver within a console, including a display and the optical light source. The remaining spectrum of the incident light continues propagation through the core fiber toward a distal end of the stylet. The remaining spectrum of the incident light may encounter other sensors from the distributed array of sensors, where each of these sensors is fabricated to reflect light with different specific spectral widths to provide distributed measurements, as described above.

During operation, multiple light reflections (also referred to as "reflected light signals") are returned to the console from each of the plurality of core fibers of the multi-core optical fiber. Each reflected light signal may be uniquely associated with a different spectral width. Information associated with the reflected light signals may be used to determine a three-dimensional representation of the physical state of the stylet within the body of a patient through detection of strain and/or an instantaneous oxygen level measurement through detection of ambient temperature variation in response to emitted incident light. Herein, the core fibers are spatially separated with the cladding of the multi-mode optical fiber and each core fiber is configured to separately return light of different spectral widths (e.g., specific light wavelength or a range of light wavelengths) reflected from the distributed array of sensors fabricated in each of the core fibers.

During vasculature insertion and advancement of the catheter, the clinician may rely on the console to visualize a current physical state (e.g., shape) of a catheter guided by the stylet to avoid potential path deviations. As the periphery core fibers reside at spatially different locations within the cladding of the multi-mode optical fiber, changes in angular orientation (such as bending with respect to the center core fiber, etc.) of the stylet imposes different types (e.g., compression or tension) and degrees of strain on each of the periphery core fibers as well as the center core fiber. The different types and/or degree of strain may cause the sensors of the core fibers to apply different wavelength shifts, which can be measured to extrapolate the physical state of the stylet (catheter).

Embodiments of the disclosure may include a combination of one or more of the methodologies to confirm that an optical fiber within a body of implementation (e.g., an introducer wire, a guidewire, a stylet within a needle, a needle with fiber optic inlayed into the cannula, a stylet configured for use with a catheter, an optical fiber between a needle and a catheter, and/or an optical fiber integrated into a catheter) is located at a specified location with the vasculature based on oximetry readings determined from light reflected from one or more sensors disposed at the distal tip of the optical fiber.

Certain embodiments of the disclosure pertain to the utilization of fiber optic shape sensing, detection of oxygen levels and/or blood flow direction to track advancement of a medical device throughout the vasculature of a patient. For example, as noted above, each core fiber includes a plurality of reflective gratings disposed along its length, wherein each reflective grating receives broadband incident light and reflects light signals having a specific spectral width (e.g., a specific wavelength or specific range of wavelengths) that may be shifted based on an amount of strain applied to a length of the core fiber corresponding to the reflective grating. The incident light also be emitted from the distal tip of a core fiber into the vasculature such that the distal tip receives light reflected from the red blood cells, which propagates back to the console.

In some embodiments in which an optical fiber is integrated into or otherwise disposed in a needle, systems and methods disclosed herein may provide alerts, such as warnings or notifications, that the needle has punctured the posterior wall of a vessel or indicate a pneumothorax. For instance, in the same manner as discussed above, the optical fiber within the needle emits incident light and receives reflected light, which is received by the console and translated reflection data. In embodiments in which the optical fiber is disposed within a needle, the reflect data may indicate that the distal tip of the needle is in a vessel based on the reflection data correlating to an expected oxygen level of either a vein or an artery. Further, such an embodiment may provide an indication that the needle has punctured the posterior wall of the vessel when the reflection data indicates a change in the oxygen level (e.g., a drastic decrease in the oxygen level, which may indicate that the distal tip of the needle is no longer in either a vein or artery).

Additionally, the optical fiber disposed within a needle may be utilized to detect a pneumothorax. Following insertion of the needle into a patient's torso, the optical fiber may emit light, detect any reflected light such that the reflected light propagates to the console for translation into reflection data and analysis. The reflection data may be correlated to known oxygen levels in order to determine the oxygen level proximate the distal tip of the optical fiber. When the distal tip of the needle (and hence the optical fiber, see FIGS. 11A-11B), logic of the console may detect pneumothorax in the patient based on determination of an anomalous oxygen level for the anatomical area near the insertion site (e.g., near the patient's lung). For example, the determined oxygen level may be greater than expected, thus indicating the presence of an abnormal collection of air in the pleural space between the lung and the chest wall.

Additionally, systems and methods disclosed may perform operations to determine whether the needle has been placed within a vein or an artery. Specifically, the logic of the console may determine that the reflection data correlates to a specific oxygen level, where such oxygen level corresponds to either a vein (e.g., lower oxygen level) or an artery (e.g., higher oxygen level).

The optical fiber disposed within a needle may also confirm a cannulated vein even in the presence of minimal or no blood return. For example, in the systems and methods disclosed, the reflection data obtained as a result of the incident light emitted from the distal tip of the optical fiber may confirm that the needle was inserted into a vein or an artery based on the determined oxygen level proximate the distal tip of the optical fiber.

Some embodiments include a medical device system for inserting a medical instrument within a patient body, where the system comprises the medical instrument including an optical fiber having one or more of core fibers. The system may also include a console including one or more processors and a non-transitory computer-readable medium having stored thereon logic, when executed by the one or more processors, causes operations including providing an incident light signal to the optical fiber, receiving a reflected light signal of the incident light, wherein the reflected light signal is reflected from at least one or red blood cells or tissue within the patient body, and processing the reflected light signal to determine an oxygen level within the patient body near a distal tip of the optical fiber.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In yet some embodiments, the optical fiber is a single-core optical fiber, and wherein the incident light is provided in pulses.

In some embodiments, the optical fiber is a multi-core optical fiber including a plurality of core fibers, and wherein the incident light propagates along a first core fiber and the reflect light signal propagates along a second core fiber. In other embodiments, determining the location of the distal tip of the optical fiber within the patient body is based on the oxygen level and an entry site of the medical instrument.

In further embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

In some embodiments, the reflected light signal indicates pneumothorax. In yet other embodiments, the medical instrument is located within a vessel of the patient body, and wherein the reflected light signal indicates a direction of blood flow. In other embodiments, the medical instrument is located within a vessel of the patient body, and wherein the reflected light signal indicates a juncture of the vessel with a second vessel based on an increase in the oxygen level. In some embodiments, the medical instrument is located within the patient body, and wherein the reflected light signal indicates a change in volume of blood between a first location within the patient body and a second location within the patient body. In some embodiments, the medical instrument is a needle and has been inserted into a vessel of the patient body, and wherein the reflected light signal indicates the needle has punctured a posterior wall of the vessel based on a decrease in the oxygen level. In other embodiments, the logic, when executed by the one or more processors, causes further operations including determining whether the optical fiber is located within an artery or a vein of the patient body based on the oxygen level.

Other embodiments of the disclosure are directed to a method for placing a medical instrument into a body of a patient. The method includes operations of providing an incident light signal to an optical fiber disposed within the medical instrument, wherein the optical fiber includes one or more core fibers, receiving a reflected light signal of the incident light, wherein the reflected light signal is reflected from at least one of red blood cells or tissue within the patient body, and processing the reflected light signal to determine an oxygen level within the patient body near a distal tip of the optical fiber.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In yet some embodiments, the optical fiber is a single-core optical fiber, and wherein the incident light is provided in pulses.

In some embodiments, the optical fiber is a multi-core optical fiber including a plurality of core fibers, and wherein the incident light propagates along a first core fiber and the reflect light signal propagates along a second core fiber. In other embodiments, determining the location of the distal tip of the optical fiber within the patient body is based on the oxygen level and an entry site of the medical instrument.

In further embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

In some embodiments, the reflected light signal indicates pneumothorax. In yet other embodiments, the medical instrument is located within a vessel of the patient body, and wherein the reflected light signal indicates a direction of blood flow. In other embodiments, the medical instrument is located within a vessel of the patient body, and wherein the reflected light signal indicates a juncture of the vessel with a second vessel based on an increase in the oxygen level. In some embodiments, the medical instrument is located within the patient body, and wherein the reflected light signal indicates a change in volume of blood between a first location within the patient body and a second location within the patient body. In some embodiments, the medical instrument is a needle and has been inserted into a vessel of the patient body, and wherein the reflected light signal indicates the needle has punctured a posterior wall of the vessel based on a decrease in the oxygen level. In other embodiments, the logic, when executed by the one or more processors, causes further operations including determining whether the optical fiber is located within an artery or a vein of the patient body based on the oxygen level.

Yet other embodiments include a non-transitory computer-readable medium having stored thereon logic that, when executed by one or more processors, causes operations including providing an incident light signal to an optical fiber disposed within the medical instrument, the optical fiber including one or more core fibers, receiving a reflected light signal of the incident light, wherein the reflected light signal is reflected from at least one of red blood cells or tissue within the patient body, and processing the reflected light signal to determine an oxygen level within the patient body near a distal tip of the optical fiber.

In some embodiments, each of the one or more core fibers includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber. In yet some embodiments, the optical fiber is a single-core optical fiber, and wherein the incident light is provided in pulses.

In some embodiments, the optical fiber is a multi-core optical fiber including a plurality of core fibers, and wherein the incident light propagates along a first core fiber and the reflect light signal propagates along a second core fiber. In other embodiments, determining the location of the distal tip of the optical fiber within the patient body is based on the oxygen level and an entry site of the medical instrument.

In further embodiments, the logic, when executed by the one or more processors, causes further operations including generating a display indicating the location of the distal tip of the optical fiber within the patient body.

In some embodiments, the medical instrument is one of an introducer wire, a guidewire, a stylet, a stylet within a needle, a needle with the optical fiber inlayed into a cannula of the needle or a catheter with the optical fiber inlayed into one or more walls of the catheter.

In some embodiments, the reflected light signal indicates pneumothorax. In yet other embodiments, the medical instrument is located within a vessel of the patient body, and wherein the reflected light signal indicates a direction of blood flow. In other embodiments, the medical instrument is located within a vessel of the patient body, and wherein the reflected light signal indicates a juncture of the vessel with a second vessel based on an increase in the oxygen level. In some embodiments, the medical instrument is located within the patient body, and wherein the reflected light signal indicates a change in volume of blood between a first location within the patient body and a second location within the patient body. In some embodiments, the medical instrument is a needle and has been inserted into a vessel of the patient body, and wherein the reflected light signal indicates the needle has punctured a posterior wall of the vessel based on a decrease in the oxygen level. In other embodiments, the logic, when executed by the one or more processors, causes further operations including determining whether the optical fiber is located within an artery or a vein of the patient body based on the oxygen level.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 3A is a first exemplary embodiment of the stylet of FIG. 1A supporting both an optical and electrical signaling in accordance with some embodiments;

FIG. 3B is a cross sectional view of the stylet of FIG. 3A in accordance with some embodiments;

FIG. 4A is a second exemplary embodiment of the stylet of FIG. 1B in accordance with some embodiments;

FIG. 4B is a cross sectional view of the stylet of FIG. 4A in accordance with some embodiments;

FIGS. 6A-6B are flowcharts of the methods of operations conducted by the medical instrument monitoring system of FIGS. 1A-1B to achieve optic 3D shape sensing in accordance with some embodiments;

DETAILED DESCRIPTION

Figure 1A:
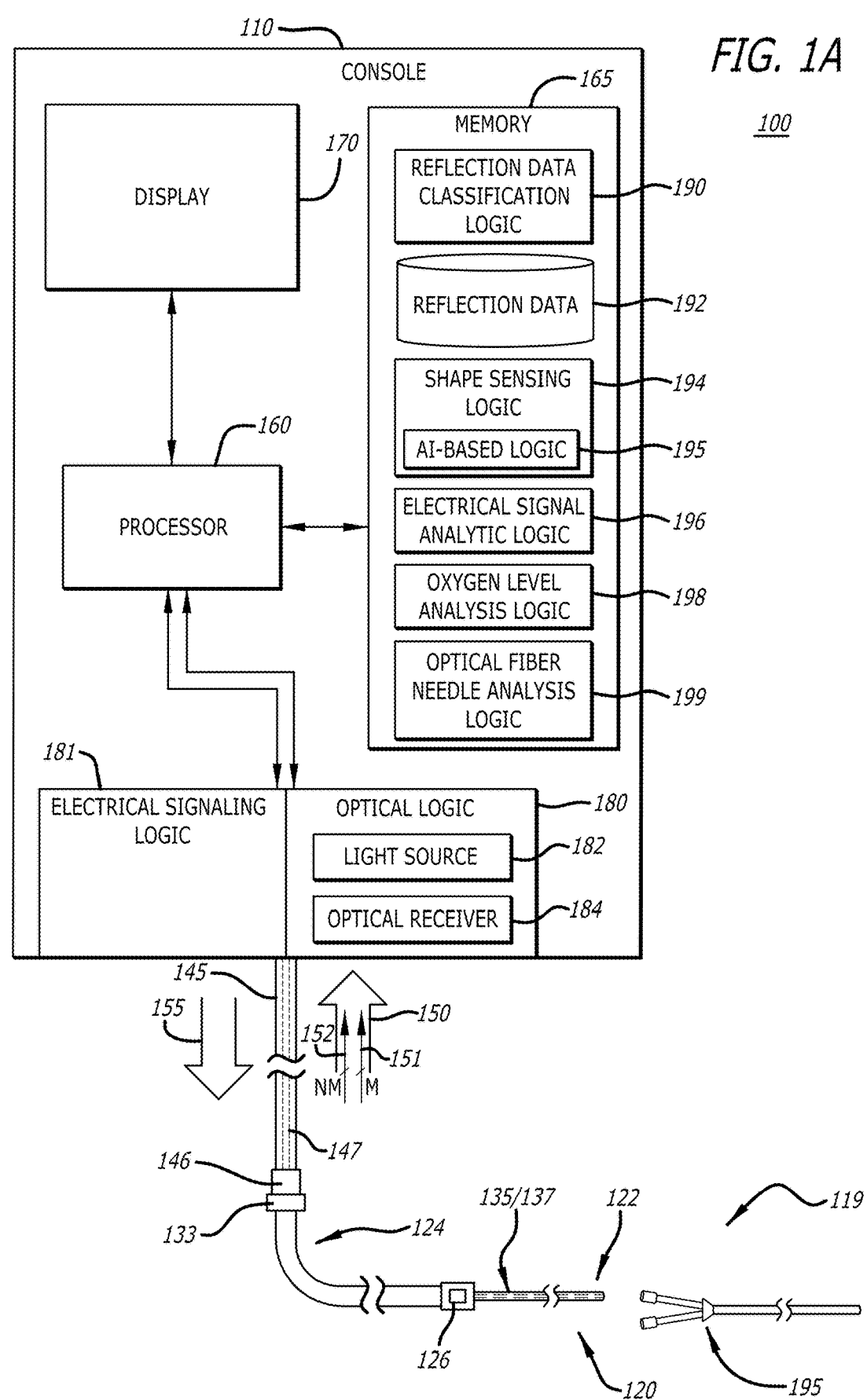
FIG. 1A is an illustrative embodiment of a medical instrument monitoring system including a medical instrument with optic shape sensing and fiber optic-based oximetry capabilities in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random-access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Referring to FIG. 1A, an illustrative embodiment of a medical instrument monitoring system including a medical instrument with optic shape sensing and fiber optic-based oximetry capabilities is shown in accordance with some embodiments. As shown, the system 100 generally includes a console 110 and a stylet assembly 119 communicatively coupled to the console 110. For this embodiment, the stylet assembly 119 includes an elongate probe (e.g., stylet) 120 on its distal end 122 and a console connector 133 on its proximal end 124, where the stylet 120 is configured to advance within a patient vasculature either through, or in conjunction with, a catheter 195. The console connector 133 enables the stylet assembly 119 to be operably connected to the console 110 via an interconnect 145 including one or more optical fibers 147 (hereinafter, "optical fiber(s)") and a conductive medium terminated by a single optical/electric connector 146 (or terminated by dual connectors). Herein, the connector 146 is configured to engage (mate) with the console connector 133 to allow for the propagation of light between the console 110 and the stylet assembly 119 as well as the propagation of electrical signals from the stylet 120 to the console 110.

An exemplary implementation of the console 110 includes a processor 160, a memory 165, a display 170 and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Pat. No. 10,992,078, the entire contents of which are incorporated by reference herein. The processor 160, with access to the memory 165 (e.g., non-volatile memory or non-transitory, computer-readable medium), is included to control functionality of the console 110 during operation. As shown, the display 170 may be a liquid crystal diode (LCD) display integrated into the console 110 and employed as a user interface to display information to the clinician, especially during a catheter placement procedure (e.g., cardiac catheterization). In another embodiment, the display 170 may be separate from the console 110. Although not shown, a user interface is configured to provide user control of the console 110.

For both embodiments, the content depicted by the display 170 may change according to which mode the stylet 120 is configured to operate: optical, TLS, ECG, or another modality. In TLS mode, the content rendered by the display 170 may constitute a two-dimensional (2D) or three-dimensional (3D) representation of the physical state (e.g., length, shape, form, and/or orientation) of the stylet 120 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below According to one embodiment of the disclosure, an activation control 126, included on the stylet assembly 119, may be used to set the stylet 120 into a desired operating mode and selectively alter operability of the display 170 by the clinician to assist in medical device placement. For example, based on the modality of the stylet 120, the display 170 of the console 110 can be employed for optical modality-based guidance during catheter advancement through the vasculature or TLS modality to determine the physical state (e.g., length, form, shape, orientation, etc.) of the stylet 120. In one embodiment, information from multiple modes, such as optical, TLS or ECG for example, may be displayed concurrently (e.g., at least partially overlapping in time).

Referring still to FIG. 1A, the optical logic 180 is configured to support operability of the stylet assembly 119 and enable the return of information to the console 110, which may be used to determine the physical state associated with the stylet 120 along with monitored electrical signals such as ECG signaling via an electrical signaling logic 181 that supports receipt and processing of the received electrical signals from the stylet 120 (e.g., ports, analog-to-digital conversion logic, etc.). The physical state of the stylet 120 may be based on changes in characteristics of the reflected light signals 150 received at the console 110 from the stylet 120. The characteristics may include shifts in wavelength caused by strain on certain regions of the core fibers integrated within an optical fiber core 135 positioned within or operating as the stylet 120, as shown below. As discussed herein, the optical fiber core 135 may be comprised of core fibers $137_1$-$137_M$ (M=1 for a single core, and M≥2 for a multi-core), where the core fibers $137_1$-$137_M$ may collectively be referred to as core fiber(s) 137. Unless otherwise specified or the instant embodiment requires an alternative interpretation, embodiments discussed herein will refer to a multi-core optical fiber 135. From information associated with the reflected light signals 150, the console 110 may determine (through computation or extrapolation of the wavelength shifts) the physical state of the stylet 120, and that of the catheter 195 configured to receive the stylet 120.

According to one embodiment of the disclosure, as shown in FIG. 1A, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the multi-core optical fiber core 135 within the stylet 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the multi-core optical fiber 135 deployed within the stylet 120, and (ii) translate the reflected light signals 150 into reflection data (from repository 192), namely data in the form of electrical signals representative of the reflected light signals including wavelength shifts caused by strain. The reflected light signals 150 associated with different spectral widths may include reflected light signals 151 provided from sensors positioned in the center core fiber (reference) of the multi-core optical fiber 135 and reflected light signals 152 provided from sensors positioned in the periphery core fibers of the multi-core optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the processor 160, which governs their operation. Also, the optical receiver 184 is operably coupled to provide the reflection data (from repository 192) to the memory 165 for storage and processing by reflection data classification logic 190. The reflection data classification logic 190 may be configured to: (i) identify which core fibers pertain to which of the received reflection data (from repository 192) and (ii) segregate the reflection data stored with a repository 192 provided from reflected light signals 150 pertaining to similar regions of the stylet 120 or spectral widths into analysis groups. The reflection data for each analysis group is made available to shape sensing logic 194 for analytics.

According to one embodiment of the disclosure, the shape sensing logic 194 is configured to compare wavelength shifts measured by sensors deployed in each periphery core fiber at the same measurement region of the stylet 120 (or same spectral width) to the wavelength shift at a center core fiber of the multi-core optical fiber 135 positioned along central axis and operating as a neutral axis of bending. From these analytics, the shape sensing logic 194 may determine the shape the core fibers have taken in 3D space and may further determine the current physical state of the catheter 195 in 3D space for rendering on the display 170.

According to one embodiment of the disclosure, the shape sensing logic 194 may generate a rendering of the current physical state of the stylet 120 (and potentially the catheter 195), based on heuristics or run-time analytics. For example, the shape sensing logic 194 may be configured in accordance with machine-learning techniques to access a data store (library) with pre-stored data (e.g., images, etc.) pertaining to different regions of the stylet 120 (or catheter 195) in which reflected light from core fibers have previously experienced similar or identical wavelength shifts. From the pre-stored data, the current physical state of the stylet 120 (or catheter 195) may be rendered. Alternatively, as another example, the shape sensing logic 194 may be configured to determine, during run-time, changes in the physical state of each region of the multi-core optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the multi-core optical fiber 135 to the wavelength shift generated by a sensor of the center core fiber at the same cross-sectional region. It is contemplated that other processes and procedures may be performed to utilize the wavelength shifts as measured by sensors along each of the core fibers within the multi-core optical fiber 135 to render appropriate changes in the physical state of the stylet 120 (and/or catheter 195), especially to enable guidance of the stylet 120, when positioned at a distal tip of the catheter 195, within the vasculature of the patient and at a desired destination within the body.

The console 110 may further include electrical signaling logic 181, which is positioned to receive one or more electrical signals from the stylet 120. The stylet 120 is configured to support both optical connectivity as well as electrical connectivity. The electrical signaling logic 181 receives the electrical signals (e.g., ECG signals) from the stylet 120 via the conductive medium. The electrical signals may be processed by electrical signal logic 196, executed by the processor 160, to determine ECG waveforms for display.

Figure 1B:
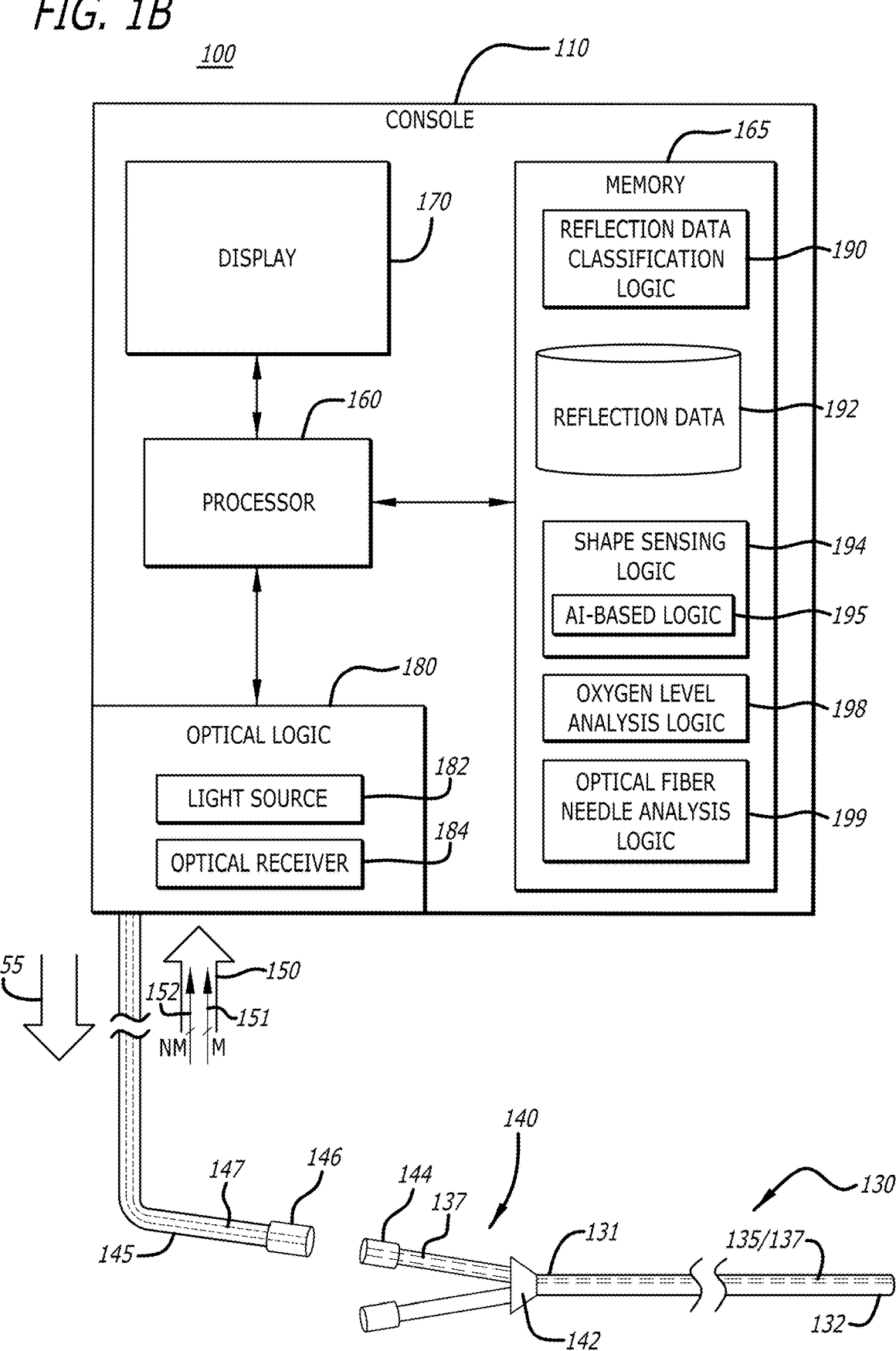
FIG. 1B is an alternative illustrative embodiment of the medical instrument monitoring system 100 in accordance with some embodiments.

Referring to FIG. 1B, an alternative exemplary embodiment of a medical instrument monitoring system 100 is shown. Herein, the medical instrument monitoring system 100 features a console 110 and a medical instrument 130 communicatively coupled to the console 110. For this embodiment, the medical instrument 130 corresponds to a catheter, which features an integrated tubing with two or more lumen extending between a proximal end 131 and a distal end 132 of the integrated tubing. The integrated tubing (sometimes referred to as "catheter tubing") is in communication with one or more extension legs 140 via a bifurcation hub 142. An optical-based catheter connector 144 may be included on a proximal end of at least one of the extension legs 140 to enable the catheter 130 to operably connect to the console 110 via an interconnect 145 or another suitable component. Herein, the interconnect 145 may include a connector 146 that, when coupled to the optical-based catheter connector 144, establishes optical connectivity between one or more optical fibers 147 (hereinafter, "optical fiber(s)") included as part of the interconnect 145 and core fibers 137 deployed within the catheter 130 and integrated into the tubing. Alternatively, a different combination of connectors, including one or more adapters, may be used to optically connect the optical fiber(s) 147 to the core fibers 137 within the catheter 130. The core fibers 137 deployed within the catheter 130 as illustrated in FIG. 1B include the same characteristics and perform the same functionalities as the core fibers 137 deployed within the stylet 120 of FIG. 1A.

The optical logic 180 is configured to support graphical rendering of the catheter 130, most notably the integrated tubing of the catheter 130, based on characteristics of the reflected light signals 150 received from the catheter 130. The characteristics may include shifts in wavelength caused by strain on certain regions of the core fibers 137 integrated within (or along) a wall of the integrated tubing, which may be used to determine (through computation or extrapolation of the wavelength shifts) the physical state of the catheter 130, notably its integrated tubing or a portion of the integrated tubing such as a tip or distal end of the tubing to read fluctuations (real-time movement) of the tip (or distal end).

More specifically, the optical logic 180 includes a light source 182. The light source 182 is configured to transmit the broadband incident light 155 for propagation over the optical fiber(s) 147 included in the interconnect 145, which are optically connected to multiple core fibers 137 within the catheter tubing. Herein, the optical receiver 184 is configured to: (i) receive returned optical signals, namely reflected light signals 150 received from optical fiber-based reflective gratings (sensors) fabricated within each of the core fibers 137 deployed within the catheter 130, and (ii) translate the reflected light signals 150 into reflection data (from repository 192), namely data in the form of electrical signals representative of the reflected light signals including wavelength shifts caused by strain. The reflected light signals 150 associated with different spectral widths include reflected light signals 151 provided from sensors positioned in the center core fiber (reference) of the catheter 130 and reflected light signals 152 provided from sensors positioned in the outer core fibers of the catheter 130, as described below.

As noted above, the shape sensing logic 194 is configured to compare wavelength shifts measured by sensors deployed in each outer core fiber at the same measurement region of the catheter (or same spectral width) to the wavelength shift at the center core fiber positioned along central axis and operating as a neutral axis of bending. From these analytics, the shape sensing logic 190 may determine the shape the core fibers have taken in 3D space and may further determine the current physical state of the catheter 130 in 3D space for rendering on the display 170.

According to one embodiment of the disclosure, the shape sensing logic 194 may generate a rendering of the current physical state of the catheter 130, especially the integrated tubing, based on heuristics or run-time analytics. For example, the shape sensing logic 194 may be configured in accordance with machine-learning techniques to access a data store (library) with pre-stored data (e.g., images, etc.) pertaining to different regions of the catheter 130 in which the core fibers 137 experienced similar or identical wavelength shifts. From the pre-stored data, the current physical state of the catheter 130 may be rendered. Alternatively, as another example, the shape sensing logic 194 may be configured to determine, during run-time, changes in the physical state of each region of the catheter 130, notably the tubing, based on at least (i) resultant wavelength shifts experienced by the core fibers 137 and (ii) the relationship of these wavelength shifts generated by sensors positioned along different outer core fibers at the same cross-sectional region of the catheter 130 to the wavelength shift generated by a sensor of the center core fiber at the same cross-sectional region. It is contemplated that other processes and procedures may be performed to utilize the wavelength shifts as measured by sensors along each of the core fibers 137 to render appropriate changes in the physical state of the catheter 130.

Figure 2:
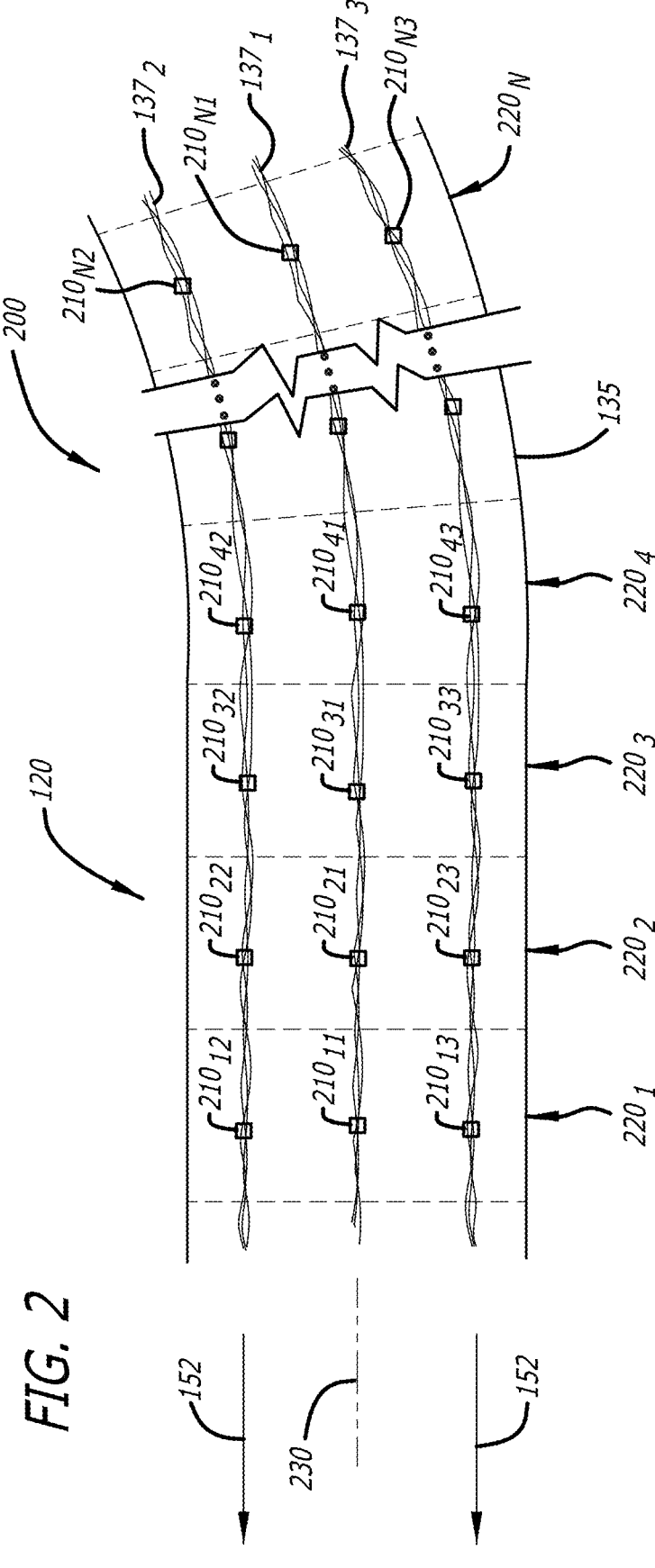
FIG. 2 is an exemplary embodiment of a structure of a section of the multi-core optical fiber included within the stylet 120 of FIG. 1A in accordance with some embodiments.

Referring to FIG. 2, an exemplary embodiment of a structure of a section of the multi-core optical fiber included within the stylet 120 of FIG. 1A is shown in accordance with some embodiments. The multi-core optical fiber section 200 of the multi-core optical fiber 135 depicts certain core fibers $137_1$-$137_M$ (M≥2, M=4 as shown, see FIG. 3A) along with the spatial relationship between sensors (e.g., reflective gratings) $210_{11}$-$210_{NM}$ (N≥2; M≥2) present within the core fibers $137_1$-$137_M$, respectively. As noted above, the core fibers $137_1$-$137_M$ may be collectively referred to as "the core fibers 137."

As shown, the section 200 is subdivided into a plurality of cross-sectional regions $220_1$-$220_N$, where each cross-sectional region $220_1$-$220_N$ corresponds to reflective gratings $210_{11}$-$210_{14}$ . . . $210_{N1}$-$210_{N4}$. Some or all of the cross-sectional regions $220_1$ . . . $220_N$ may be static (e.g., prescribed length) or may be dynamic (e.g., vary in size among the regions $220_1$ . . . $220_N$). A first core fiber $137_1$ is positioned substantially along a center (neutral) axis 230 while core fiber $137_2$ may be oriented within the cladding of the multi-core optical fiber 135, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$. As examples, FIGS. 3A-4B provides illustrations of such.

Referencing the first core fiber $137_1$ as an illustrative example, when the stylet 120 is operative, each of the reflective gratings $210_1$-$210_N$ reflects light for a different spectral width. As shown, each of the gratings $210_{1i}$-$210_{Ni}$ (1≤i≤M) is associated with a different, specific spectral width, which would be represented by different center frequencies of $f_1$ . . . $f_N$, where neighboring spectral widths reflected by neighboring gratings are non-overlapping according to one embodiment of the disclosure.

Herein, positioned in different core fibers $137_2$-$137_3$ but along at the same cross-sectional regions $220$-$220_N$ of the multi-core optical fiber 135, the gratings $210_{12}$-$210_{N2}$ and $210_{13}$-$210_{N3}$ are configured to reflect incoming light at same (or substantially similar) center frequency. As a result, the reflected light returns information that allows for a determination of the physical state of the optical fibers 137 (and the stylet 120) based on wavelength shifts measured from the returned, reflected light. In particular, strain (e.g., compression or tension) applied to the multi-core optical fiber 135 (e.g., at least core fibers $137_2$-$137_3$) results in wavelength shifts associated with the returned, reflected light. Based on different locations, the core fibers $137_1$-$137_4$ experience different types and degree of strain based on angular path changes as the stylet 120 advances in the patient.

For example, with respect to the multi-core optical fiber section 200 of FIG. 2, in response to angular (e.g., radial) movement of the stylet 120 is in the left-veering direction, the fourth core fiber $137_4$ (see FIG. 3A) of the multi-core optical fiber 135 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fibers $137_2$ and $137_3$ will exhibit different changes in wavelength. The differences in wavelength shift of the reflected light signals 150 can be used to extrapolate the physical configuration of the stylet 120 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the multi-core optical fiber 135. These degrees of wavelength change may be used to extrapolate the physical state of the stylet 120. The reflected light signals 150 are reflected back to the console 110 via individual paths over a particular core fiber $137_1$-$137_M$.

Referring to FIG. 3A, a first exemplary embodiment of the stylet of FIG. 1A supporting both an optical and electrical signaling is shown in accordance with some embodiments. Herein, the stylet 120 features a centrally located multi-core optical fiber 135, which includes a cladding 300 and a plurality of core fibers $137_1$-$137_M$ (M≥2; M=4) residing within a corresponding plurality of lumens $320_1$-$320_M$. While the multi-core optical fiber 135 is illustrated within four (4) core fibers $137_1$-$137_4$, a greater number of core fibers $137_1$-$137_M$ (M≥4) may be deployed to provide a more detailed three-dimensional sensing of the physical state (e.g., shape, etc.) of the multi-core optical fiber 135 and the stylet 120 deploying the optical fiber 135.

For this embodiment of the disclosure, the multi-core optical fiber 135 is encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the stylet 120, as a greater spacing may provide a lesser rigidity, and thereby, a more pliable stylet 120.

According to this embodiment of the disclosure, as shown in FIGS. 3A-3B, the core fibers $137_1$-$137_4$ include (i) a central core fiber $137_1$ and (ii) a plurality of periphery core fibers $137_2$-$137_4$, which are maintained within lumens $320_1$-$320_4$ formed in the cladding 300. According to one embodiment of the disclosure, one or more of the lumens $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the multi-core optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_2$-$320_4$ each formed within different areas of the cladding 300 radiating from the first neutral axis 230. In general, the core fibers $137_2$-$137_4$, exclusive of the central core fiber $137_1$, may be positioned at different areas within a cross-sectional area 305 of the cladding 300 to provide sufficient separation to enable three-dimensional sensing of the multi-core optical fiber 135 based on changes in wavelength of incident light propagating through the core fibers $137_2$-$137_4$ and reflected back to the console for analysis.

For example, where the cladding 300 features a circular cross-sectional area 305 as shown in FIG. 3B, the core fibers $137_2$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3A-3B, operating as the conductive medium for the stylet 120, the braided tubing 310 provides mechanical integrity to the multi-core optical fiber 135 and operates as a conductive pathway for electrical signals. For example, the braided tubing 310 may be exposed to a distal tip of the stylet 120. The cladding 300 and the braided tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both for the cladding 300 and the braided tubing 310, as shown.

Referring to FIG. 4A, a second exemplary embodiment of the stylet of FIG. 1A is shown in accordance with some embodiments. Herein, the stylet 120 features the multi-core optical fiber 135 described above and shown in FIG. 3A, which includes the cladding 300 and the first plurality of core fibers $137_1$-$137_M$ (M≥3; M=4 for embodiment) residing within the corresponding plurality of lumens $320_1$-$320_M$. For this embodiment of the disclosure, the multi-core optical fiber 135 includes the central core fiber $137_1$ residing within the first lumen $320_1$ formed along the first neutral axis 230 and the second plurality of core fibers $137_2$-$137_4$ residing within corresponding lumens $320_2$-$320_4$ positioned in different segments within the cross-sectional area 305 of the cladding 300. Herein, the multi-core optical fiber 135 is encapsulated within a conductive tubing 400. The conductive tubing 400 may feature a "hollow" conductive cylindrical member concentrically encapsulating the multi-core optical fiber 135.

Referring to FIGS. 4A-4B, operating as a conductive medium for the stylet 120 in the transfer of electrical signals (e.g., ECG signals) to the console, the conductive tubing 400 may be exposed up to a tip 410 of the stylet 120. For this embodiment of the disclosure, a conductive epoxy 420 (e.g., metal-based epoxy such as a silver epoxy) may be affixed to the tip 410 and similarly joined with a termination/connection point created at a proximal end 430 of the stylet 120. The cladding 300 and the conductive tubing 400, which is positioned concentrically surrounding a circumference of the cladding 300, are contained within the same insulating layer 440. The insulating layer 440 may be a protective conduit encapsulating both for the cladding 300 and the conductive tubing 400, as shown.

Figures 5A, 5B:
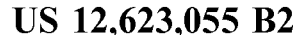
FIG. 5A is an elevation view of a first illustrative embodiment of a catheter including integrated tubing, a diametrically disposed septum, and micro-lumens formed within the tubing and septum in accordance with some embodiments.
FIG. 5B is a perspective view of the first illustrative embodiment of the catheter of FIG. 5A including core fibers installed within the micro-lumens in accordance with some embodiments.

Referring to FIG. 5A, an elevation view of a first illustrative embodiment of a catheter including integrated tubing, a diametrically disposed septum, and micro-lumens formed within the tubing and septum is shown in accordance with some embodiments. Herein, the catheter 130 includes integrated tubing, the diametrically disposed septum 510, and the plurality of micro-lumens $530_1$-$530_4$ which, for this embodiment, are fabricated to reside within the wall 500 of the integrated tubing of the catheter 130 and within the septum 510. In particular, the septum 510 separates a single lumen, formed by the inner surface 505 of the wall 500 of the catheter 130, into multiple lumens, namely two lumens 540 and 545 as shown. Herein, the first lumen 540 is formed between a first arc-shaped portion 535 of the inner surface 505 of the wall 500 forming the catheter 130 and a first outer surface 555 of the septum 510 extending longitudinally within the catheter 130. The second lumen 545 is formed between a second arc-shaped portion 565 of the inner surface 505 of the wall 500 forming the catheter 130 and a second outer surfaces 560 of the septum 510.

According to one embodiment of the disclosure, the two lumens 540 and 545 have approximately the same volume. However, the septum 510 need not separate the tubing into two equal lumens. For example, instead of the septum 510 extending vertically (12 o'clock to 6 o'clock) from a front-facing, cross-sectional perspective of the tubing, the septum 510 could extend horizontally (3 o'clock to 9 o'clock), diagonally (1 o'clock to 7 o'clock; 10 o'clock to 4 o'clock) or angularly (2 o'clock to 10 o'clock). In the later configuration, each of the lumens 540 and 545 of the catheter 130 would have a different volume.

With respect to the plurality of micro-lumens $530_1$-$530_4$, the first micro-lumen $530_1$ is fabricated within the septum 510 at or near the cross-sectional center 525 of the integrated tubing. For this embodiment, three micro-lumens $530_2$-$530_4$ are fabricated to reside within the wall 500 of the catheter 130. In particular, a second micro-lumen $530_2$ is fabricated within the wall 500 of the catheter 130, namely between the inner surface 505 and outer surface 507 of the first arc-shaped portion 535 of the wall 500. Similarly, the third micro-lumen $530_3$ is also fabricated within the wall 500 of the catheter 130, namely between the inner and outer surfaces 505/507 of the second arc-shaped portion 555 of the wall 500. The fourth micro-lumen $530_4$ is also fabricated within the inner and outer surfaces 505/507 of the wall 500 that are aligned with the septum 510.

According to one embodiment of the disclosure, as shown in FIG. 5A, the micro-lumens $530_2$-$530_4$ are positioned in accordance with a "top-left" (10 o'clock), "top-right" (2 o'clock) and "bottom" (6 o'clock) layout from a front-facing, cross-sectional perspective. Of course, the micro-lumens $530_2$-$530_4$ may be positioned differently, provided that the micro-lumens $530_2$-$530_4$ are spatially separated along the circumference 520 of the catheter 130 to ensure a more robust collection of reflected light signals from the outer core fibers $570_2$-$570_4$ when installed. For example, two or more of micro-lumens (e.g., micro-lumens $530_2$ and $530_4$) may be positioned at different quadrants along the circumference 520 of the catheter wall 500.

Referring to FIG. 5B, a perspective view of the first illustrative embodiment of the catheter of FIG. 5A including core fibers installed within the micro-lumens is shown in accordance with some embodiments. According to one embodiment of the disclosure, the second plurality of micro-lumens $530_2$-$530_4$ are sized to retain corresponding outer core fibers $570_2$-$570_4$, where the diameter of each of the second plurality of micro-lumens $530_2$-$530_4$ may be sized just larger than the diameters of the outer core fibers $570_2$-$570_4$. The size differences between a diameter of a single core fiber and a diameter of any of the micro-lumen $530_1$-$530_4$ may range between 0.001 micrometers (μm) and 1000 μm, for example. As a result, the cross-sectional areas of the outer core fibers $570_2$-$570_4$ would be less than the cross-sectional areas of the corresponding micro-lumens $530_2$-$530_4$. A "larger" micro-lumen (e.g., micro-lumen $530_2$) may better isolate external strain being applied to the outer core fiber $570_2$ from strain directly applied to the catheter 130 itself. Similarly, the first micro-lumen $530_1$ may be sized to retain the center core fiber $570_1$, where the diameter of the first micro-lumen $530_1$ may be sized just larger than the diameter of the center core fiber $570_1$.

As an alternative embodiment of the disclosure, one or more of the micro-lumens $530_1$-$530_4$ may be sized with a diameter that exceeds the diameter of the corresponding one or more core fibers $570_1$-$570_4$. However, at least one of the micro-lumens $530_1$-$530_4$ is sized to fixedly retain their corresponding core fiber (e.g., core fiber retained with no spacing between its lateral surface and the interior wall surface of its corresponding micro-lumen). As yet another alternative embodiment of the disclosure, all the micro-lumens $530_1$-$530_4$ are sized with a diameter to fixedly retain the core fibers $570_1$-$570_4$.

Figure 6A:
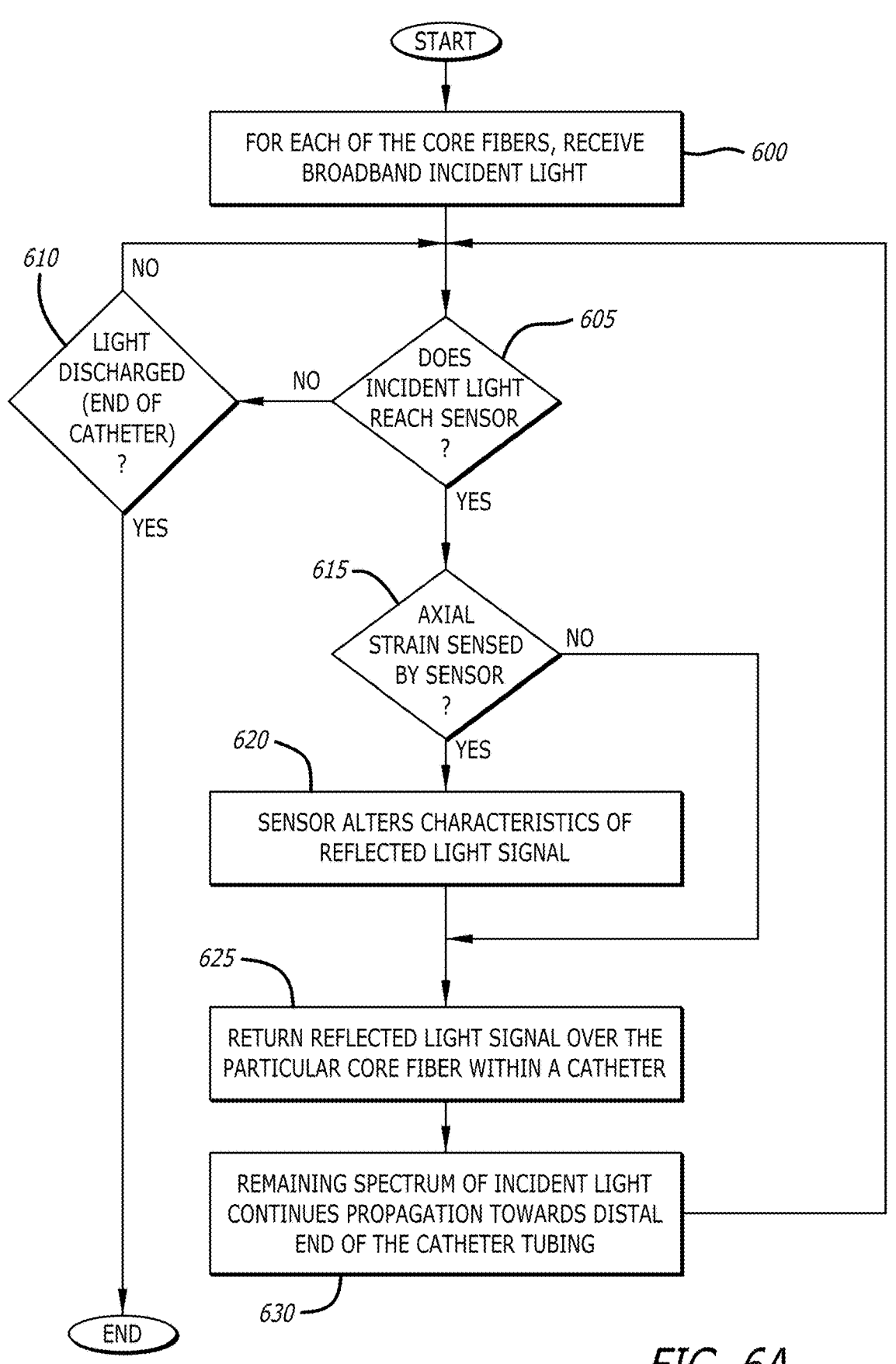

Referring to FIGS. 6A-6B, flowcharts of methods of operations conducted by the medical instrument monitoring system of FIGS. 1A-1B to achieve optic 3D shape sensing are shown in accordance with some embodiments. Herein, the catheter includes at least one septum spanning across a diameter of the tubing wall and continuing longitudinally to subdivide the tubing wall. The medial portion of the septum is fabricated with a first micro-lumen, where the first micro-lumen is coaxial with the central axis of the catheter tubing. The first micro-lumen is configured to retain a center core fiber. Two or more micro-lumen, other than the first micro-lumen, are positioned at different locations circumferentially spaced along the wall of the catheter tubing. For example, two or more of the second plurality of micro-lumens may be positioned at different quadrants along the circumference of the catheter wall.

Furthermore, each core fiber includes a plurality of sensors spatially distributed along its length between at least the proximal and distal ends of the catheter tubing. This array of sensors is distributed to position sensors at different regions of the core fiber to enable distributed measurements of strain throughout the entire length or a selected portion of the catheter tubing. These distributed measurements may be conveyed through reflected light of different spectral widths (e.g., specific wavelength or specific wavelength ranges) that undergoes certain wavelength shifts based on the type and degree of strain.

According to one embodiment of the disclosure, as shown in FIG. 6A, for each core fiber, broadband incident light is supplied to propagate through a particular core fiber (block 600). Unless discharged, upon the incident light reaching a sensor of a distributed array of sensors measuring strain on a particular core fiber, light of a prescribed spectral width associated with the first sensor is to be reflected back to an optical receiver within a console (blocks 605-610). Herein, the sensor alters characteristics of the reflected light signal to identify the type and degree of strain on the particular core fiber as measured by the first sensor (blocks 615-620). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the catheter tubing (blocks 625-630). The remaining spectrum of the incident light may encounter other sensors of the distributed array of sensors, where each of these sensors would operate as set forth in blocks 605-630 until the last sensor of the distributed array of sensors returns the reflected light signal associated with its assigned spectral width and the remaining spectrum is discharged as illumination.

Referring now to FIG. 6B, during operation, multiple reflected light signals are returned to the console from each of the plurality of core fibers residing within the corresponding plurality of micro-lumens formed within a catheter, such as the catheter of FIG. 1B. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 650-655). The reflection data classification logic is configured to identify which core fibers pertain to which reflection data and segregate reflection data provided from reflected light signals pertaining to a particular measurement region (or similar spectral width) into analysis groups (block 660-665).

Each analysis group of reflection data is provided to shape sensing logic for analytics (block 670). Herein, the shape sensing logic compares wavelength shifts at each outer core fiber with the wavelength shift at the center core fiber positioned along central axis and operating as a neutral axis of bending (block 675). From these analytics, on all analytic groups (e.g., reflected light signals from sensors in all or most of the core fibers), the shape sensing logic may determine the shape the core fibers have taken in three-dimensional space, from which the shape sensing logic can determine the current physical state of the catheter in three-dimension space (blocks 680-685).

Figure 7:
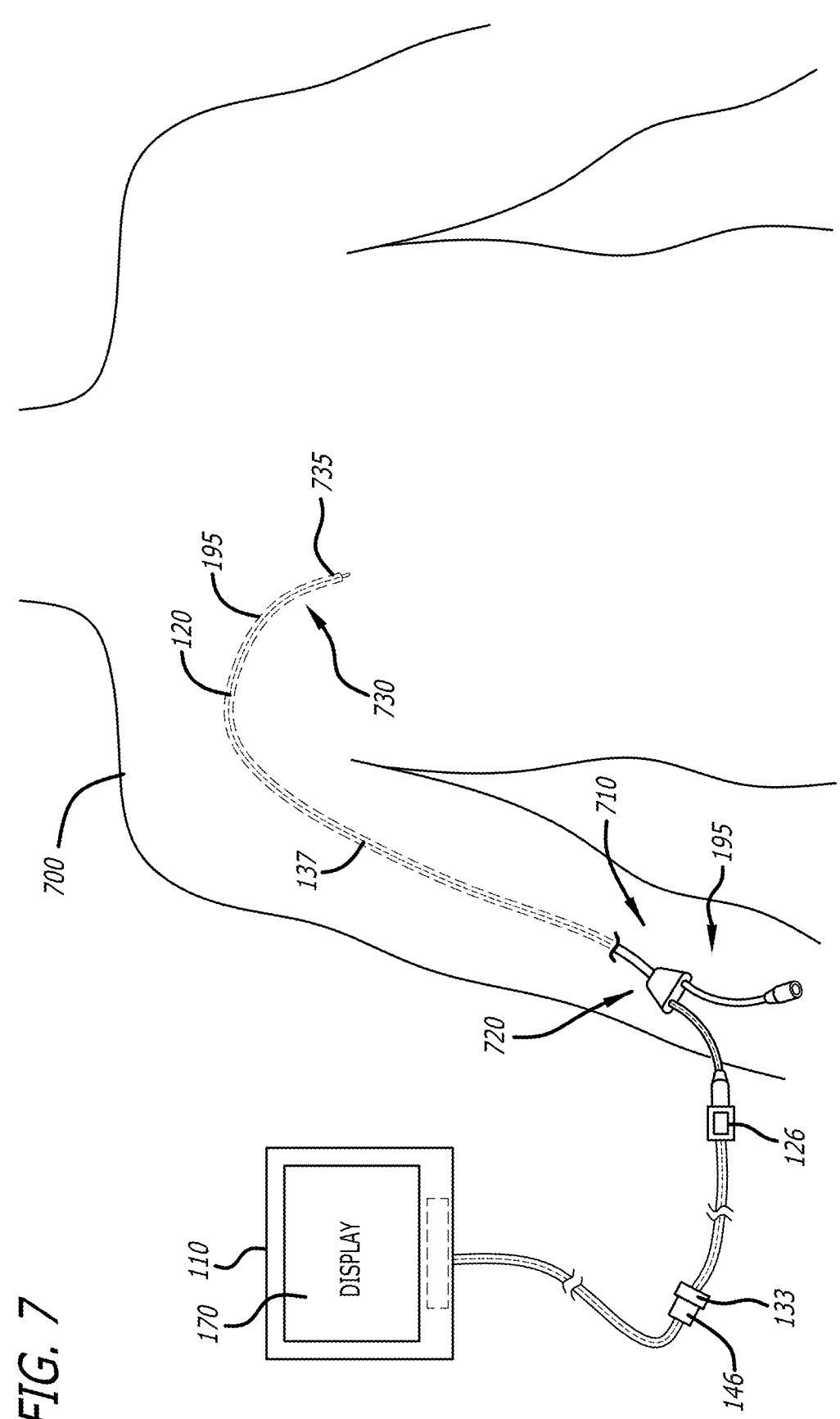
FIG. 7 is an exemplary embodiment of the medical instrument monitoring system of FIG. 1A during operation and insertion of the catheter into a patient in accordance with some embodiments.

Referring to FIG. 7, an exemplary embodiment of the medical instrument monitoring system of FIG. 1A during operation and insertion of the catheter into a patient are shown in accordance with some embodiments. Herein, the catheter 195 generally includes integrated tubing with a proximal portion 720 that generally remains exterior to the patient 700 and a distal portion 730 that generally resides within the patient vasculature after placement is complete, where the catheter 195 enters the vasculature at insertion site 710. The stylet 120 may be advanced through the catheter 195 to a desired position within the patient vasculature such that a distal end (or tip) 735 of the stylet 120 (and hence a distal end of the catheter 195) is proximate the patient's heart, such as in the lower one-third (⅓) portion of the Superior Vena Cava ("SVC") for example. For this embodiment, various instruments may be placed at the distal end 735 of the stylet 120 and/or the catheter 195 to measure pressure of blood in a certain heart chamber and in the blood vessels, view an interior of blood vessels, or the like.

The console connector 133 enables the stylet 120 to be operably connected to the console 110 via the interconnect 145 (FIG. 1A). Herein, the connector 146 is configured to engage (mate) with the console connector 133 to allow for the propagation of light between the console 110 and the stylet assembly 119 (particularly the stylet 120) as well as the propagation of electrical signals from the stylet 120 to the console 110.

Figures 8A, 8B:
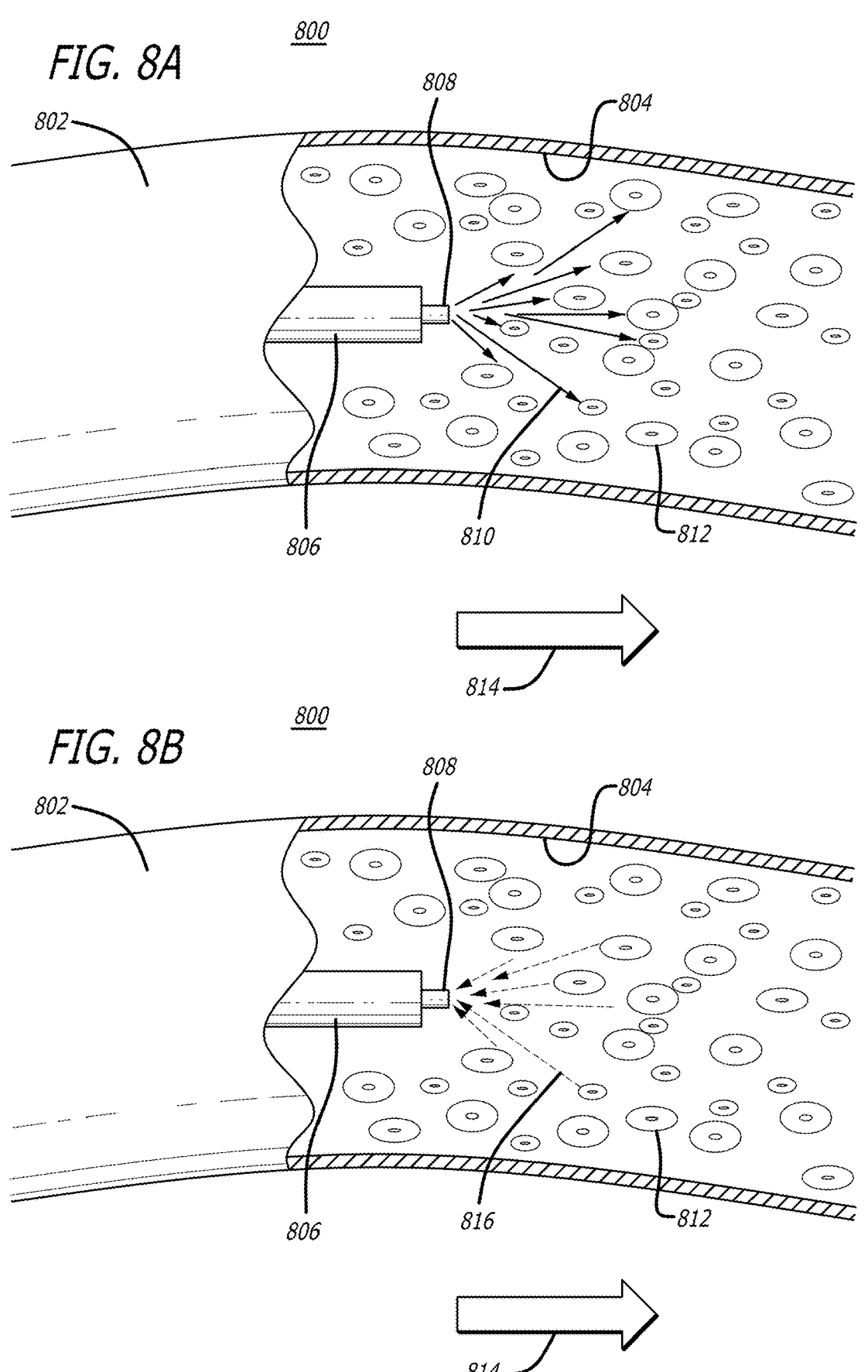
FIG. 8A is a cross sectional perspective view of a vessel within a vasculature having a medical instrument advancing therein where the medical instrument includes an optical fiber shown to be emitting light from a distal tip in accordance with some embodiments.
FIG. 8B is a cross sectional perspective view of the vessel of FIG. 8A having the medical instrument advancing therein where the distal tip of the optical fiber is shown as receiving light reflected by red blood cells in accordance with some embodiments.

Referring now to FIG. 8A, a cross sectional perspective view of a vessel within a vasculature having a medical instrument advancing therein where the medical instrument includes an optical fiber shown to be emitting light from a distal tip is shown in accordance with some embodiments. The cross-sectional perspective view of the vessel 802 illustrates an interior 804 containing blood flow including red blood cells 812. Additionally, FIG. 8A illustrates that a medical instrument, e.g., a catheter or stylet, 806 is advancing through the vessel 802, where the medical instrument 806 includes an optical fiber 808 disposed therein. The optical fiber 808 may include one or more core fibers, with each core fiber configured to receive incident light from a console, e.g., the light source 182 of the console 110, such that the incident light propagates to the distal end of the core fiber and is emitted at the distal tip of the core fiber. As shown, the incident light 810 has propagated the length of a core fiber of the optical fiber 808 and is being emitted from the distal tip. A portion of the incident light 810 is absorbed by oxygen molecules of the red blood cells 812.

Referring to FIG. 8B, a cross sectional perspective view of the vessel of FIG. 8A having the medical instrument advancing therein where the distal tip of the optical fiber is shown as receiving light reflected by red blood cells is shown in accordance with some embodiments. While a portion of the emitted incident light 810 is absorbed by oxygen molecules with the red blood cells 812, a portion of the emitted incident light 810 is reflected off of the red blood cells, which is illustrated at reflected light 816. As discussed above, the reflected light 816 is detected by the distal tip of the core fiber of the optical fiber 808 and propagates the length of the core fiber to the console 110. The reflected light 816 is received by the optical receiver 184, which is configured to: (i) receive returned optical signals, e.g., the reflected light signals 816, and (ii) translate the reflected light signals 816 into reflection data, namely data in the form of electrical signals representative of the reflected light signals 816.

The oxygen level analysis logic 198 subsequently analyzes the reflection data to determine an oxygen level within the blood flowing through the vessel 802 at a location proximate the distal tip of the optical fiber 808. Specifically, the amount of incident light 810 that is absorbed by the oxygen molecules may affect the light waves included in the reflected light 816. For example, oxygen molecules within the red blood cells 812 may absorb a particular wavelength range, e.g., a subset of a wavelength range of substantially 550-650 nm, such that the lack of such wavelengths (or a decrease in the amount of such wavelengths) may be detected by the oxygen level analysis logic 198. The oxygen level analysis logic 198 may determine a level of absorption from the reflection data and correlate the level of absorption with oxygen levels to determine the oxygen level of the blood flowing through the vessel 802 at a location proximate the distal tip of the optical fiber 808. In one embodiment, the level of absorption may correspond to a ratio of the incident light 810 to the reflected light 816. In some embodiments, the level of absorption may be correlated with experiential data comprising known levels of absorption with each indicating a particular oxygen level.

The determined oxygen level may be utilized in determining a location of the distal tip of the optical fiber 808 within the vasculature. For example, certain oxygen levels may correspond to particular locations within the vasculature such that, based on an insertion site and, optionally other location or navigation data (e.g., the shape sensing functionality discussed above, detection of blood flow direction, ECG, etc.), a location of the distal tip of the optical fiber 808 may be determined or at least approximated to be within a certain range of the vasculature. For example, the determined oxygen level may provide an indication that the distal tip of the optical fiber 808 (and hence the distal tip of the medical instrument 806) has deviated from its intended path of advancement (e.g., out of the SVC and into the Azygos vein).

In addition to determining the oxygen level, the oxygen level analysis logic 198 may also analyze the reflection data to determine the direction of the flow of blood, where the direction of flow is indicated by the arrow 814 in FIGS. 8A-8B. The reflected light 816 is affected by the direction of the flow as there is less light reflected to the distal tip of the optical fiber 808 when the flow of blood is away from the distal tip of the optical fiber 808 (e.g., in the direction of advancement of the optical fiber 808) as opposed to when the flow of blood is coming toward the distal tip of the optical fiber 808 (e.g., opposite the direction of advancement of the optical fiber 808). Thus, based on the intensity of the reflected light 816, the oxygen level analysis logic 198 may determine the direction of the flow of blood. Any of the determinations performed by the logic of the oxygen level analysis logic 198 may be provided to a clinician through alerts or notifications via the console 110, e.g., via the display 170 or via speakers (not shown). Additionally, the alerts or notifications may be transmitted to a network device, such as a mobile phone, a tablet, wearable technology, etc.

Figures 9, 10:
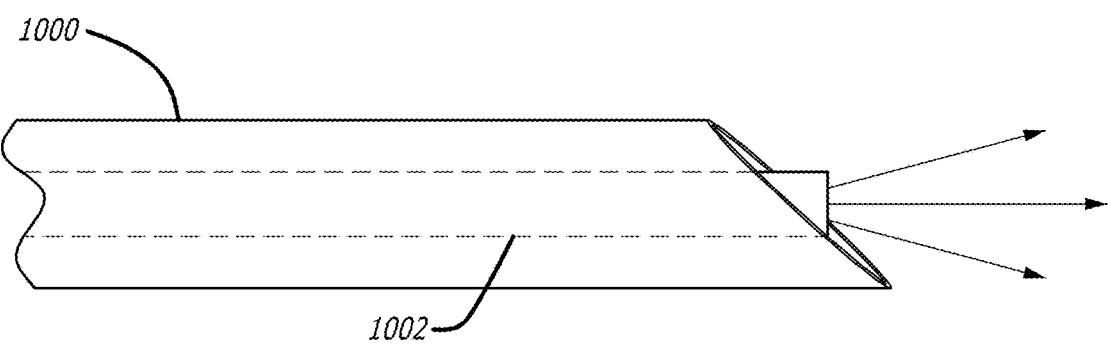
FIG. 9 is a cross sectional perspective view of vessel of FIG. 8A illustrated at a juncture with a branching vessel and having the medical instrument advancing therein where the medical instrument includes an optical fiber shown to be emitting light from a distal tip in accordance with some embodiments.
FIG. 10 is an embodiment of a needle including an optical fiber disposed therein where the optical fiber is shown to be emitting light from a distal tip in accordance with some embodiments.

Referring to FIG. 9, a cross sectional perspective view of vessel of FIG. 8A illustrated at a juncture with a branching vessel and having the medical instrument advancing therein where the medical instrument includes an optical fiber shown to be emitting light from a distal tip is shown in accordance with some embodiments. The vessel 802 is shown as a point along its length that includes the juncture 904 where the branching vessel 902 meets the vessel 802. As in FIGS. 8A-8B, the arrow 814 indicates the direction of the flow of blood. Embodiments of the disclosure may be utilized to detect a juncture 904 within a vessel 802 due to a change in the blood flow, e.g., a change in the amount of blood. For example, the optical fiber 808 detects reflected light ("reflected light_A") while advancing through the vessel 802 in portion A, and detects reflected light ("reflected light_B") while advancing through the vessel 802 in portion B. As the reflected light_A will differ from reflected light_B, the oxygen level analysis logic 198 may note the change and determine that the distal tip of the optical fiber 808 is advancing past a juncture. For example, as FIG. 9 illustrates, red blood cells entering the vessel 802 from the branching vessel 902 increase the number of red blood cells to reflect the incident light 810. Therefore, based on the increase in incident light 810 that is reflected, as opposed to being absorbed or propagating through the vessel wall, the juncture 904 may be identified.

In some embodiments, the identification of a juncture may enable a clinician to track the advancement of the optical fiber 808 (and hence the medical instrument 806) through the vessel 802 using junctures as a marking system against a known anatomy. By way of example, the reflected light may indicate spikes in oxygen levels during advancement through a particular vessel such that each spike may be determined to correspond to a vessel junction. Thus, each spike in oxygen levels may correspond to a marker as the optical fiber is advanced. Any of the determinations performed by the logic of the oxygen level analysis logic 198 may be provided to a clinician through alerts or notifications via the console 110, e.g., via the display 170 or via speakers (not shown). Additionally, the alerts or notifications may be transmitted to a network device, such as a mobile phone, a tablet, wearable technology, etc.

Referring now to FIG. 10, an embodiment of a needle including an optical fiber disposed therein where the optical fiber is shown to be emitting light from a distal tip is shown in accordance with some embodiments. The needle 1000 is shown as including an optical fiber 1002 disposed therein. As will be discussed below with respect to FIGS. 11A-11B, the optical fiber 10002 of the needle 1000 may be used to determine proper cannulation of a vessel via emission of incident light from the distal tip of the optical fiber 1002 and detection of light reflected from red blood cells.

Figure 11A:
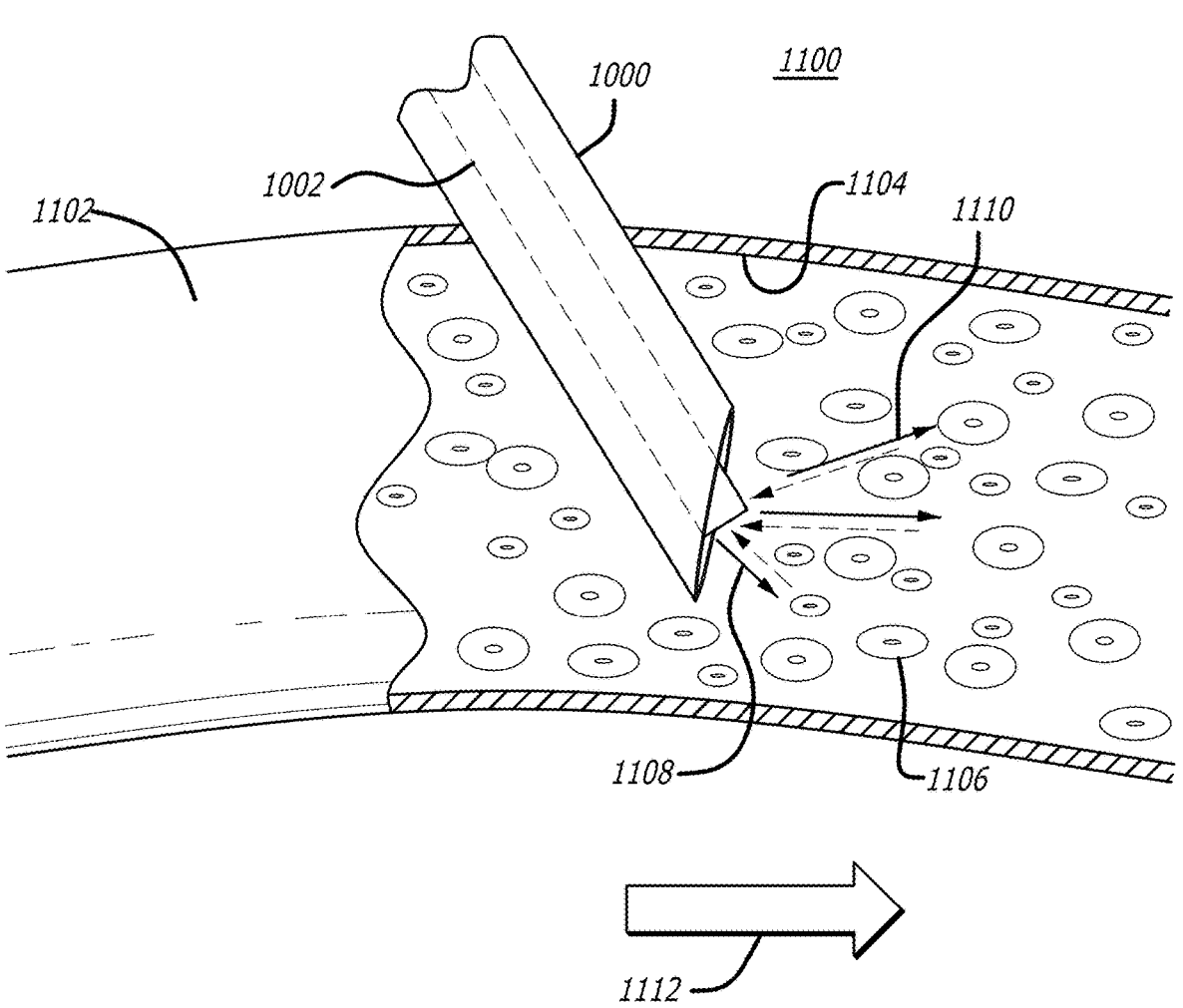
FIG. 11A is a cross sectional perspective view of a vessel including an entry puncture by the needle of FIG. 10 in accordance with some embodiments.

Referring now to FIG. 11A, a cross sectional perspective view of a vessel including an entry puncture by the needle of FIG. 10 is shown in accordance with some embodiments. The vasculature environment 1100 is illustrated as including a vessel 1102 that is cannulated by the needle 1000 of FIG. 10. As discussed above with respect to FIGS. 8A-9, the optical fiber 1002 within the needle 1000 may be configured to receive incident light 1108 from a console, e.g., the light source 182 of the console 110, such that the incident light 1108 is emitted from the distal tip of the optical fiber 1002. As shown in FIG. 11A, the optical fiber 1002 may be utilized to confirm proper cannulation by emitting incident light 1108 and receiving reflected light 1110. The reflected light 1110 may propagate back to the console 110 and be translated into reflection data, which is then analyzed by the optical fiber needle analysis logic 199. The analysis of the reflected may confirm proper cannulation when the reflected light 1110 closely correlates to the expected reflection data for a proper cannulation. In some embodiments, the optical fiber needle analysis logic 199 may determine an oxygen level based on a correlation of the reflection data to known oxygen levels. The optical fiber needle analysis logic 199 may then determine whether the oxygen level corresponds to a known oxygen level of the intended target vessel.

When the oxygen level corresponds (e.g., substantially matches, or is within a particular threshold of the expected, known oxygen level), the optical fiber needle analysis logic 199 determines proper cannulation has occurred. Similarly, the optical fiber needle analysis logic 199 may utilize the determined oxygen level to determine whether the needle tip has entered a vein or an artery. Veins and arteries has distinct oxygen levels; thus, the optical fiber needle analysis logic 199 may compare the determined oxygen level to known or expected oxygen levels of each of a vein and an artery (or known oxygen levels of various veins and arteries) to determine which the determined oxygen level most closely corresponds.

In most instances, a cannulated vein will result in minimal blood return either back through a needle lumen or externally proximate the entry site of the needle. The blood return may provide an indicate to a clinician that the needle has been inserted into a vein or artery. However, in some instances, there is no blood return, or the return is so minimal that it goes undetected by a clinician. In such instances, a clinician may remove a properly inserted needle. However, in the system and methods disclosed, the reflection data obtained as a result of the incident light emitted from the distal tip of the optical fiber may confirm that the needle was inserted into a vein or an artery based on the determined oxygen level proximate the distal tip of the optical fiber.

Figure 11B:
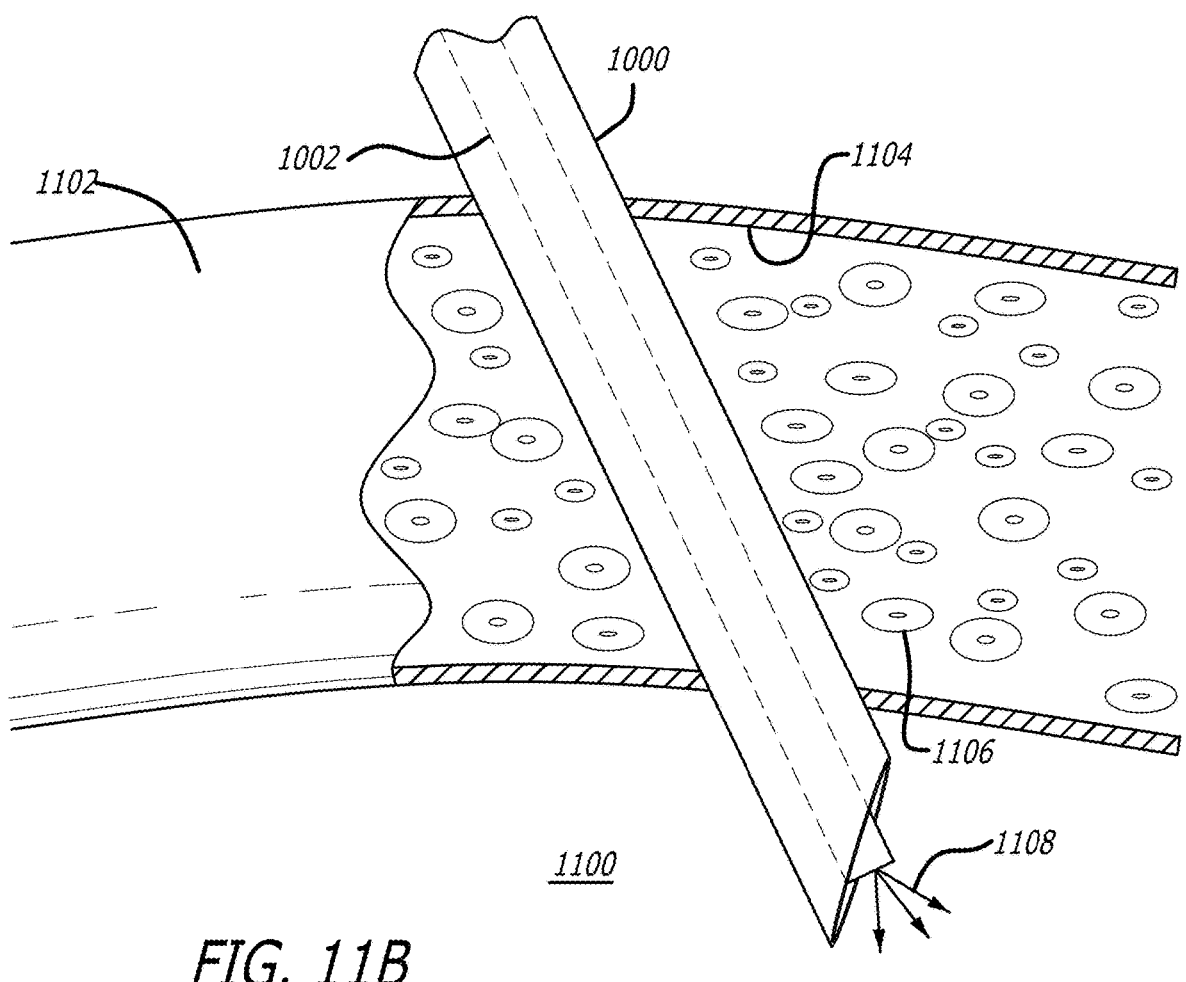
FIG. 11B is a cross sectional perspective view of the vessel of FIG. 11A including an entry puncture and an exit puncture by the needle of FIG. 10 in accordance with some embodiments.

Referring to FIG. 11B, a cross sectional perspective view of the vessel of FIG. 11A including an entry puncture and an exit puncture by the needle of FIG. 10 is shown in accordance with some embodiments. In contrast to the illustration of a proper cannulation of FIG. 11A, FIG. 11B illustrates the needle 1000 has passed through the vessel 1102 such that the distal tip of the needle 1000 has punctured the vessel wall opposite the entry point. As shown, the incident light 1108 emitted from the optical fiber 1002 may not be reflected back (or a received reflection may be different and distinguishable from light reflected from red blood cells, as in FIG. 11A). Thus, due to the lack of reflected light received at the console 110, the optical fiber needle analysis logic 199 may determine that the needle 1000 has exited the vessel 1102. One or more alerts may be generated indicating improper cannulation. These alerts may be audio or visual notifications and may be displayed on the display 170 or otherwise provided by the console 110.

Any of the determinations performed by the logic of the optical fiber needle analysis logic 199 may be provided to a clinician through alerts or notifications via the console 110, e.g., via the display 170 or via speakers (not shown). Additionally, the alerts or notifications may be transmitted to a network device, such as a mobile phone, a tablet, wearable technology, etc.

In any of the embodiments of FIG. 8A-11B discussed above and in the method 1200 discussed below, the optical fiber may include a single core fiber or a plurality of core fibers. When a single core fiber is included, the incident light may be transmitted in pulses so that a pulse may be propagated from the console to the distal tip of the core fiber, the pulse may be emitted, and reflected light may be returned back to the console. When a plurality of core fibers are included, the incident light may be transmitted in the distal direction over a first core fiber and transmitted in a proximal direction over a second core fiber.

Figure 12:
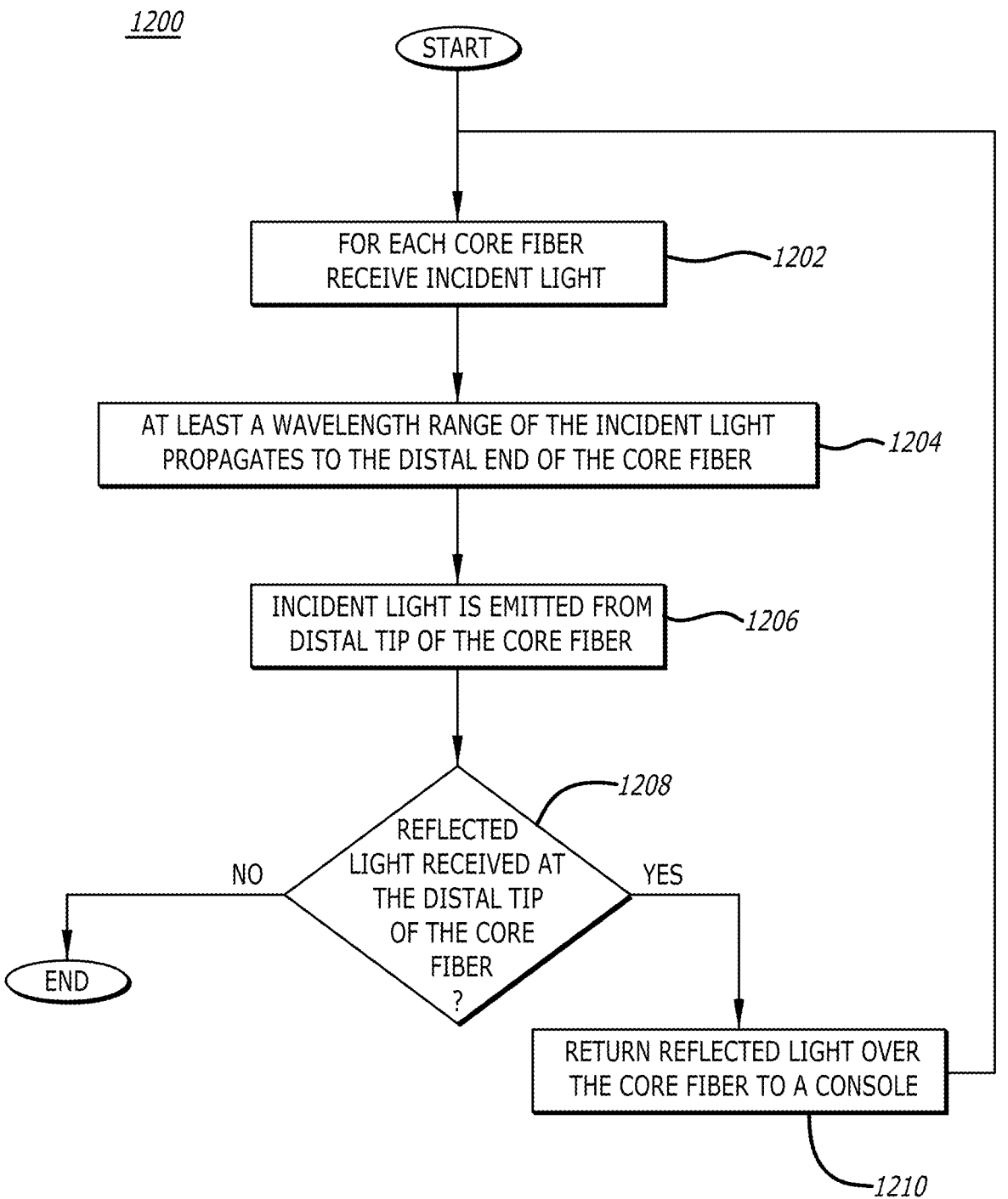
FIG. 12 is a flowchart illustrating an exemplary method of operations conducted by the medical instrument monitoring system of either of FIGS. 1A-1B deploying the medical instrument and optical fiber of FIGS. 8A-9 in accordance with some embodiments

Referring to FIG. 12, a flowchart illustrating an exemplary method of operations conducted by the medical instrument monitoring system of either of FIGS. 1A-1B deploying the medical instrument and optical fiber of FIGS. 8A-9 are shown in accordance with some embodiments. Prior to initiation of the method 1200, it is assumed that a medical instrument having an optical fiber disposed therein is advancing through a vasculature of a patient. Each block illustrated in FIG. 12 represents an operation performed in the method 1200, which is initiated when a core fiber receives incident light from a light source of a console (block 1202). The incident light propagates to a distal end of the core fiber (block 1204). In some embodiments, at least a particular wavelength range of the incident light propagates to the distal end while some wavelength ranges are reflected back by reflective gratings as discussed above with respect to the shape sensing functionality.

The incident light that propagates to the distal end of the core fiber is emitted from the distal tip of the core fiber (block 1206). As discussed above, the emitted incident light collides with red blood cells with certain wavelengths being absorbed by oxygen molecules with the red blood cells. It should be understood that blood traveling in arteries (oxygen-rich blood) will absorb a greater amount of incident light than blood that is traveling in veins (blood low in oxygen). When light is reflected from the red blood cells and detected by the distal tip of the core fiber, the reflected light is returned over the core fiber to the console (blocks 1208-1210). As discussed above, logic stored in and processed by the console analyses the received reflected light to perform one or more determinations related to oxygen levels, juncture determinations, location determinations or confirmations, blood flow direction detection, etc.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A non-transitory computer-readable medium having stored thereon logic that, when executed by one or more processors, causes operations including:
   providing an incident light signal to an optical fiber of a medical instrument, the optical fiber having one or more core fibers;
   receiving a reflected light signal of the incident light signal, wherein the reflected light signal is reflected from one or more of red blood cells or tissue within a patient body into which the medical instrument is inserted;
   processing the reflected light signal to determine an oxygen level within the patient body near a distal tip of the optical fiber, and
   determining a location of the distal tip of the optical fiber within the patient body based on the oxygen level and an entry site of the medical instrument.

2. The non-transitory computer-readable medium according to claim 1, wherein each of the one or more core fibers includes a plurality of sensors distributed along a longitudinal length thereof, and wherein each sensor of the plurality of sensors is configured to (i) reflect a light signal of a different spectral width based on received incident light, and (ii) change a characteristic of the reflected light signal for use in determining a physical state of the optical fiber.

3. The non-transitory computer-readable medium according to claim 1, wherein the optical fiber is a single-core optical fiber, and wherein providing the incident light signal includes providing the incident light signal in pulses.

4. The non-transitory computer-readable medium according to claim 1, wherein the optical fiber is a multi-core optical fiber including a plurality of core fibers, and wherein a first core fiber of the plurality of core fibers is configured to propagate the incident light signal and a second core fiber of the plurality of core fibers is configured to propagate the reflected light signal.

5. The non-transitory computer-readable medium according to claim 1, wherein determining the location of the distal tip of the optical fiber within the patient body is further based on knowledge of advancement of the medical instrument.

6. The non-transitory computer-readable medium according to claim 1, wherein the logic which, when executed by the one or more processors, is configured to cause further operations including generating a display indicating the location of the distal tip of the optical fiber within the patient body.

7. The non-transitory computer-readable medium according to claim 1, wherein the medical instrument is one of an introducer wire, a guidewire, a stylet, a needle with the optical fiber inlayed into a cannula of the needle or a catheter with the optical fiber inlayed into one or more walls of the catheter.

8. The non-transitory computer-readable medium according to claim 1, wherein the logic which, when executed by the one or more processors, is configured to cause further operations including detecting pneumothorax through detection of an anomalously high oxygen level.

9. The non-transitory computer-readable medium according to claim 1, wherein the medical instrument is configured to be placed within a vessel of the patient body, and wherein the logic which, when executed by the one or more processors, is configured to cause further operations including detecting a direction of blood flow based on an intensity of the reflected light signal.

10. The non-transitory computer-readable medium according to claim 1, wherein the medical instrument is configured to be placed within a vessel of the patient body, and wherein the logic which, when executed by the one or more processors, is configured to cause further operations including detecting a juncture of the vessel with a second vessel based on an increase in the oxygen level as indicated by the reflected light signal.

11. The non-transitory computer-readable medium according to claim 1, wherein the logic which, when executed by the one or more processors, is configured to cause further operations including detecting a change in intensity of the reflected light signal from a first intensity to a second intensity, wherein the change from the first intensity to the second intensity indicates a change in volume of blood between a first location within the patient body and a second location within the patient body.

12. The non-transitory computer-readable medium according to claim 1, wherein the medical instrument is a needle and is configured to be placed into a vessel of the patient body, and wherein the logic which, when executed by the one or more processors, is configured to cause further operations including detecting a first change in an intensity of the reflected light signal indicating an entry puncture by the needle with respect to the vessel and detecting a second change in the intensity of the reflected light signal indicating an exit puncture with respect to a posterior wall of the vessel.

13. The non-transitory computer-readable medium according to claim 1, wherein the logic which, when executed by the one or more processors, is configured to cause further operations including determining whether the optical fiber is located within an artery or a vein of the patient body based on the oxygen level.

* * * * *